(12) United States Patent
Young et al.

(10) Patent No.: US 8,545,888 B2
(45) Date of Patent: Oct. 1, 2013

(54) TENDON STEM CELLS

(75) Inventors: Marian F. Young, Silver Spring, MD (US); Yanming Bi, Boyds, MD (US); Songtao Shi, Irvine, CA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 453 days.

(21) Appl. No.: 12/663,663

(22) PCT Filed: Jun. 13, 2008

(86) PCT No.: PCT/US2008/007426
§ 371 (c)(1),
(2), (4) Date: Sep. 7, 2010

(87) PCT Pub. No.: WO2008/156685
PCT Pub. Date: Dec. 24, 2008

(65) Prior Publication Data
US 2010/0330182 A1    Dec. 30, 2010

Related U.S. Application Data

(60) Provisional application No. 60/934,606, filed on Jun. 14, 2007.

(51) Int. Cl.
| | |
|---|---|
| *A61K 35/32* | (2006.01) |
| *A61K 9/00* | (2006.01) |
| *A61K 38/17* | (2006.01) |
| *C12N 5/071* | (2010.01) |
| *C12N 5/074* | (2010.01) |
| *A61P 19/08* | (2006.01) |
| *A61P 19/04* | (2006.01) |
| *A61P 19/00* | (2006.01) |
| *A61P 29/00* | (2006.01) |
| *A61P 19/02* | (2006.01) |
| *A61P 17/00* | (2006.01) |
| *A61P 21/00* | (2006.01) |

(52) U.S. Cl.
USPC ........... 424/484; 435/325; 435/377; 435/375; 424/93.7; 514/16.7

(58) Field of Classification Search
None
See application file for complete search history.

(56) References Cited

U.S. PATENT DOCUMENTS

2006/0263774 A1 * 11/2006 Clark et al. ............... 435/6

FOREIGN PATENT DOCUMENTS

| WO | WO2007/080591 | * | 7/2007 |
| WO | WO 2007/080591 A1 | | 7/2007 |

OTHER PUBLICATIONS

Bakker et al. "Osteoblast Isolation from Murine Calvariae and Long Bones." 2003; 80(I): 19-28).*
Salingcarboriboon et al. (Experimental Cell Research. 2003; 287: 289-300).*
Krampera et al. (Bone. 2006; 39: 678-683).*
Kolf et al. (Arthritis Research & Therapy, published online Feb. 19, 2007; 9: 204).*
Ameye et al. (May 2002) FASEB Journal, 16(7):673-680, "Abnormal collagen fibrils in tendons of biglycan/fibromodulin-deficient mice lead to gait impairment, ectopic ossification, and osteoarthritis".
Barrilleaux et al. (Nov. 2006) Tissue Engineering, 12(11):3007-3019, "Review: Ex vivo engineering of living tissues with adult stem cells".
Bi et al. (Oct. 2007) Nature Medicine, 13(10):1219-1227, "Identification of tendon stem/progenitor cells and the role of the extracellular matrix in their niche".
Ringe et al. (Aug. 2002) Naturwissenschaften, 89(8):338-351, "Stem Cells for Regenerative Medicine: Advances in the Engineering of Tissues and Organs".
Rios et al. (Mar. 2007) Techniques in Orthopaedics, 22(1):2-9, "Biologics in shoulder surgery: The role of adult mesenchymal stem cells in tendon repair".
Salingcarnboriboon et al. (Jan. 2003) Experimental Cell Research, 287:289-300, "Establishment of Tendon-derived Cell Lines Exhibiting Pluripotent Mesenchymal Stem Cell-like Property".
Smith et al. (Sep. 2005) British Journal of Sports Medicine, 39(9):582-584.

* cited by examiner

*Primary Examiner* — Scott Long
(74) *Attorney, Agent, or Firm* — Swanson & Bratschun, L.L.C

(57) ABSTRACT

The invention relates to tendon stem cell useful for treating a variety of diseases and conditions, including tendon repair and attachment of tendon to bone. The invention is also directed to treatment and/or inhibition of bone formation by use of biglycan and/or fibromodulin.

21 Claims, 25 Drawing Sheets

Ectopic bone in tendon normal patella

WT controls

Bgn/fmodDKO

TENDON STEM CELLS

CROSS-REFERENCE TO RELATED APPLICATIONS

This application is a 35 USC §371 of PCT Application No. PCT/US2008/007426, filed Jun. 13, 2008, currently pending, entitled "Tendon Stem Cells," which claims priority to U.S. Provisional Application No. 60/934,606, filed Jun. 14, 2007, the contents of which are specifically incorporated herein in their entirety.

SEQUENCE LISTING

Incorporated by reference herein in its entirety is the Sequence Listing entitled "6137NIDCR-4-PUS Sequence Listing Project_ST25.txt," created Sep. 7, 2010, size 30 kilobytes.

FIELD OF THE INVENTION

The present invention relates to tendon stem cells and the use of small leucine-rich proteoglycans to control the fate of these tendon stem cells.

BACKGROUND OF THE INVENTION

Tendons are specialized tissues that connect bone to muscle transmitting forces generated by muscles to allow body movement. Tendon injuries due to trauma and overuse are a common clinical problem. Damaged tendon heals very slowly and rarely attains the structural integrity and mechanical strength of normal undamaged tendon. Sharma, P. & Maffulli, N., *J. Musculoskelet. Neuronal Interact.*, 6(18):1-90 (2006). The development of new treatment options for injured tendons has been hindered because of our limited understanding of the basic tendon biology. Id.

The primary unit of tendon is comprised of collagen fibrils that cross-link to each other in a staggered fashion to form fibers. Tendon cells reside in between long parallel chains of the collagen fibrils and synthesize a unique extracellular matrix (ECM) that contains primarily collagens, large proteoglycans, and small leucine-rich proteoglycans (SLRPs), which function as lubricators and as organizers for collagen fibril assembly. Despite the large presence of the extracellular matrix in tendon, very little is known about its role in regulating the function of cells that reside within it. A better understanding of the mechanisms that regulate the function and the differentiation of tendon cells is essential to developing new treatments for tendinopathy such as tendon rupture or ectopic ossification due to injury from overuse or from trauma.

Moreover, many types of tissues are subject to the effects of aging, and become deficient over time. One effect of aging is the loss of elasticity in tissue. This affects the appearance of the tissue and its function. While various lotions and medicaments are available for treatment of the effects of aging, none of them are particularly effective. For example, lotions and creams containing collagen are available but without the ability to form functional collagen fibrils, such collagen creams are not particularly effective for improving the elasticity of skin and other tissues. Thus, the effects of aging and age-related tissue problems are often related to a deficit of functional cell types. Lower cell populations and changing gene expression patterns can alter the elasticity, resilience, recovery from injury, cell proliferation, cell differentiation, signaling pathways, feedback mechanisms, and tissue homeostasis, amongst other physiological processes.

Accordingly, a need exists for more insight into tendon cells and methods for regulating tendon cell function, growth and differentiation. Also a need exists for improving the elasticity, resilience, and recovery from injury in aging tissues, as well as repairing injured or diseased tissues, especially elastic tissues such as tendons.

SUMMARY OF THE INVENTION

According to the invention, the adult tendon contains a population of cells that have stem cell characteristics and can form tendons in vivo. This was demonstrated by showing the cells were clonogenic, multipotent, and highly regenerative (over 20 population doublings) in vitro and in vivo. The tendon stem cells can form tendon structures that can attach to bone in vivo and that form enthesis-like structures.

Thus, the tendon stem cells have the potential to be used for tendon tissue repair of the tendon-bone junction. Using animal models deficient in two major components of tendon, biglycan and fibromodulin, the inventors have shown that tendon stem cell fate can be controlled by these extra-cellular matrix proteoglycans. Thus, the invention involves tendon stem cells that can be cultivated and maintained to form tendon. The small proteoglycans biglycan and fibromodulin can assist the tendon stem cells, for example, by protecting and maintaining the stem cells.

One aspect of the invention is an enriched population of isolated stem cells, wherein the stem cells are enriched from an extracellular matrix niche within tendon tissue, and can give rise to progeny consisting of two or more cell types, wherein at least one of the cell types is tendon.

Another aspect of the invention is an isolated non-embryonic stem cell that can differentiate into tendon tissue in vivo.

The enriched population of stem cells and the isolated stem cells of the invention are adult stem cells.

The enriched population of stem cells and the isolated stem cells of the invention can be isolated from tendon tissue. In some embodiments, the enriched population of stem cells and the isolated stem cells of the invention are isolated from the tendon tissue extracellular matrix. In general, the enriched population of stem cells and the isolated stem cells of the invention remain undifferentiated in culture.

One highly useful aspect of the invention is that the enriched population of stem cells and the isolated stem cells of the invention can differentiate into tendon tissue when in contact with extracellular matrix components in vivo. In addition, the enriched population of stem cells and the isolated stem cells of the invention form tendon tissue that can attach to bone. In other embodiments, the enriched population of stem cells and the isolated stem cells of the invention can differentiate into ligament and/or bone-forming cells. To generate bone-forming cells, the stem cells are exposed to bone morphogenetic protein 2 (BMP2). In further embodiments, the enriched population of stem cells and the isolated stem cells of the invention can give rise to osteogenesis, adipogenesis, chondrogenesis, or any combination thereof, in a mammal.

The enriched population of stem cells and the isolated stem cells of the invention also express higher levels of scleraxis, tenomodulin and/or tenascin C than bone marrow stromal cells. However, the enriched population of stem cells and the isolated stem cells of the invention express insignificant levels of CD34 (a hematopoietic stem cell marker), CD117 (a hematopoietic stem cell marker), CD45 (a leukocyte marker), c-kit (an endothelial cell marker), CD106 (an endothelial cell marker), CD18 (bone marrow stromal cell marker), and/or any combination thereof. Moreover, the enriched population of stem cells and the isolated stem cells of the invention express Stro-1, CD146 (Muc18), CD90, CD44, and/or any combination thereof. In addition, the enriched populations of stem cells and/or the stem cell of the present invention can express stem cell antigen-1 (Sca-1).

Another aspect of the invention is a differentiated progeny cell obtained from the enriched population of stem cells or an isolated stem cell of the invention, wherein the progeny cell is an osteoblast, odontoblast, dentin-producing cell, chondrocyte, tendon cell, ligament cell, cartilage-producing cell, adipocyte, fibroblast or a combination thereof.

Another aspect of the invention is a composition comprising a carrier and an enriched population of the present stem cells, a population of the isolated stem cells of the invention and/or a population of differentiated progeny cells derived from the present stem cells. In some embodiments the compositions of the invention can also include biglycan and/or fibromodulin. Biglycan and/or fibromodulin can, for example, protect the stem cells and/or allow expansion of the tendon stem cells. Biglycan and/or fibromodulin may also influence the differentiation of at least a portion of the tendon stem cells.

One type of carrier that can be used for the compositions of the invention is a culture medium. Other examples of carriers that can be used include a saline solution, a buffered saline solution, gelatin, polyvinyl sponges, collagen, hydroxyapatite/tricalcium phosphate and/or extracellular matrix.

Another aspect of the invention is a method of treating a defect in a patient comprising: expanding a culture of tendon stem cells in vitro to form cultured cells, collecting the cultured cells for introduction into the patient, and depositing the cultured cells at or near the defect in the patient, wherein the tendon stem cells comprise the stem cell of the invention and/or an enriched population of the present stem cells, a population of the isolated stem cells of the invention and/or a population of differentiated progeny cells derived from the present stem cells. In some embodiments, the tendon stem cells are autologous to the patient. For example, the tendon stem cells can be isolated from a healthy tendon of the patient.

In some embodiments expanding the culture of tendon stem cells comprises culturing the tendon stem cells in a culture medium comprising extracellular matrix components, for example, biglycan and/or fibromodulin and/or collagen. In some embodiments, the extracellular components are used to protect the stem cells and/or facilitate expansion of the tendon stem cell population. In other embodiments, the extracellular matrix components can inhibit differentiation of at least a portion of the tendon stem cells.

One type of defect that can be treated using the compositions and methods of the invention is a tendon condition or disease. Such a tendon condition or disease can be an anterior cruciate ligament injury, tendonitis, tendon rupture, severed or torn tendon, Achille's tendonitis, torn or ruptured Achille's tendon, rotator cuff tendonitis, bursitis, retrocalcaneal bursitis, tenosynovitis, club foot, psoriatic arthritis, rheumatoid arthritis, jumper's knee, tendon injury arising from overuse or trauma, and combinations thereof.

Other defects involve, for example, skin laxness, skin thinning, hypertrophic scars, wound, burn, hernia, breast deficiency, ligament tear, muscle tear, a periodontal disorder, a periodontal disease, and sphincter structure deficiency.

Another aspect of the invention is a method of generating bone-forming cells comprising treating the composition of the present stem cells with BMP-2 to thereby generate bone-forming cells. In some embodiments, the method also involves transplanting the bone-forming cells into a mammal. For example, by administering the composition with the BMP2 to a mammal.

Another aspect of the invention is a method of treating undesired bone formation in a mammal comprising administering an effective amount of biglycan and/or fibromodulin to thereby treat undesired bone formation in the mammal. Such an undesired bone formation can involve fibrodysplasia ossificans progressive.

Another aspect of the invention is a method of expanding and at the same time inhibiting differentiation of a population of tendon stem cells, the method comprising ex vivo culturing the tendon stem cells. In some embodiments, extracellular matrix components such as biglycan and/or collagen (e.g., collagen type I) and/or fibromodulin are used. Such extracellular matrix components can protect the stem cells and/or facilitate expansion of the tendon stem cells. In some embodiments, the extracellular matrix components can inhibit differentiation of at least a portion of the tendon stem cells.

DESCRIPTION OF THE FIGURES

FIG. 1A shows the colony-forming efficiency of murine and human tendon-derived cells. The results shown are the mean±SEM of 3-4 flasks. FIG. 1B shows cell colonies formed from 2000 murine and human tendon-derived cells after 20 days of culture in a 25 cm$^2$ flask stained with 1% saturated methyl violet. FIG. 1C shows phase contrast microscopic images to reveal the morphology of colonies formed from bone marrow-derived and tendon-derived murine and human cells. Bar=100 µm. FIG. 1D illustrates RT-PCR results showing gene expression profiles related to tendon, cartilage and bone by murine or human TSPCs and bone marrow stromal cells (BMSCs) that were cultured in the presence or absence of bone morphogenetic protein 2 (BMP2) or TGF-β for 7 days. FIG. 1E illustrates results of immunocytochemistry experiments showing the expression of proteins related to tendon and cartilage in murine TSPCs and BMSCs. Bars=50 µm. FIG. 1F shows a flow cytometry analysis illustrating the expression of cell surface markers related to stem cells, BMSCs, hematopoietic stem cells and endothelial cells on murine and human TSPCs. FIG. 1G shows a flow cytometry analysis where expression of CD90.2 was observed on the cell surfaces of murine TSPCs.

FIG. 2A illustrates the osteogenic and adipogenic differentiation of murine (left) and human (right) TSPCs. Osteogenic differentiation was assessed by measuring the accumulation of $Ca^{2+}$ 4 weeks after cells were cultured in osteogenic induction medium. $Ca^{2+}$ that accumulated in the culture was stained with alizarin red S. Adipogenic differentiation was assessed by lipid accumulation in cells after 3 weeks of induction in adipogenic induction medium. Lipid accumulated in the culture was stained with oil red O. Bar=100 µm. RT-PCR results shown below the stained cells indicated that the gene expression profiles of TSPCs were related to osteogenesis (osteo) and adipogenesis (adipo). FIG. 2B illustrates osteogenic differentiation of putative murine and human TSPCs, as detected by measuring the accumulation of $Ca^{2+}$ 4 weeks after cells were cultured in osteogenic induction medium. Bar=500 µm. The symbol * indicates a p value <0.0007. FIG. 2C shows adipogenic differentiation as assessed by measuring lipid accumulation in cells after 3 weeks of induction in adipogenic induction medium. Bar=100 µm. The symbol * indicates a p value <0.0007 and the symbol ** indicates a p value <0.02 for TSPCs vs. BMSCs. FIG. 2D illustrates the chondrogenesis differentiation of murine (right) and human (left) TSPCs. Chondrogenic differentiation was induced by culturing pelleted TSPCs in the chondrogenic induction medium for 3 weeks and assessed by toluidine blue, safranin O and the expression of aggrecan and type II collagen. Bar=100 µm. FIG. 2E illustrates the morphology, adipogenic osteogenic and chondrogenic differentiation potential of individual human TSPC clones. Dark bars=100 µm. White bar=µm. FIG. 2F illustrates the multipotential differentiation of TSPCs in vivo. TSPCs were cultured in vitro for 2 weeks in the presence of 100 ng/ml BMP2 and then transplanted with hydroxyapatite-tricalcium phosphate (HA-TCP). FIG. 2F1 shows H&E stained sections of the transplant after 8 weeks, indicating that bone, bone marrow, tendon-like tissue and fibrocartilage (FC) were formed. Bar=100 µm. Higher magnification of the upper left boxed area in FIG. 2F1 shows the presence of bone and tendon-like tissues by H&E staining (FIG. 2F2) and by polarized light (FIG. 2F3). Bars=25 µm. Fibrocartilage tissues within the larger boxed area in FIG. 2F1 was shown by alcian blue staining (FIG. 2F4, inside the dashed line) of the cartilage-like tissues and by type I collagen staining (FIG. 2F5, outside of the dashed line). Bars=100 µm. The symbol * indicates a p value <0.001, and the symbol ** indicates a p value <0.02 for TSPCs vs. BMSCs. FIG. 2G illustrates the multipotential differentiation of mouse TSPCs in vivo. TSPCs were cultured in vitro for 2 weeks in the presence of 100 ng/ml BMP2 and then transplanted with hydroxyapatite-tricalcium phosphate (HA-TCP) ceramic powder subcutaneously into an immunocompromised mouse. Goldner's trichrome staining showed bone (arrows), bone marrow, tendon-like tissue, and fibrocartilage (FC) formed after 8 weeks. Bars=50 µm.

FIG. 3A shows proliferation of murine and human TSPCs and BMSCs from the same donor as measured by BrdU incorporation. Data shown are the mean±SEM of 5-6 fields. The symbol * indicates a p value of <0.0005 for TSPCs vs. BMSCs. FIG. 3B illustrates the population doublings of multi-colony derived murine and human TSPCs and BMSCs from the same donor. Data are the mean±SEM of 3 mice or 2 donors. The symbol * indicates that the p value <0.05 for TSPCs vs. BMSCs. FIG. 3C illustrates the population doublings of single-colony derived murine and human TSPCs. FIG. 3D shows the strategy for testing the self-renewal capability of TSPCs. FIG. 3E shows TSPCs from GFP-transgenic mice formed tendon-like tissues (light dashed line) after being expanded in vitro ($8 \times 10^4$ to $12 \times 10^6$ cells) and transplanted with GELFOAM®. Immunohistochemical staining for GFP confirmed that tendon-like tissues were formed from donor cells (arrows). Bars=25 µm. FIG. 3F shows phase-contrast (upper panel) and fluorescent microscopy (lower panel) images to illustrate the morphology and GFP fluorescence of the colonies formed from transplant-derived cells. Bars=200 µm. FIG. 3G shows the colonies stained with rabbit anti-GFP antibody (rabbit IgG as negative control) and counterstained with hematoxylin (left panel). Bar=500 µm. The total number of colonies (methyl violet stained) was determined, and 90% of these colonies were GFP-positive (left panel). N.S., not significant, total colonies vs. GFP+ colonies. FIG. 3H shows that transplant-derived TSPCs maintained their multi-differentiation capacity towards osteogenesis (bar=500 µm), adipogenesis (bar=200 µm) and chondrogenesis (type II collagen positive, bar=200 µm) in vitro and tendon formation (polarized light dashed line, bar=25 µm) in vivo after being expanded in vitro ($9 \times 10^4$ to $4 \times 10^6$ cells).

FIG. 4C shows that human TSPCs formed tendon-like tissue in vivo 8 weeks after transplantation with HA/TCP (left 2 panels) and MATRIGEL® (right 2 panels). Bars=50 µm. FIG. 4D illustrates the regeneration potential of individual human TSPC clones. Tendon-like tissues (dashed lines) were formed in vivo 8 weeks after being expanded in vitro and transplantation with GELFOAM®. Tendon-like tissues were visualized by H&E staining and polarized light (polar), Bars=25 µm. FIG. 4E shows that murine BMP2-treated TSPCs formed bone-tendon junction-like tissue in vivo 8 weeks after transplantation with HA/TCP. Bars=100 µm. FIG. 4F shows that human TSPCs formed Sharpey's fibers (arrows) that were inserted into the calvarial bone after transplantation with HA/TCP on the surface of calvariae for 8 weeks. Bars=25 µm.

FIG. 5A shows that DNA label-retaining cells were surrounded by the extracellular matrix, indicating that dividing cells are largely present in the extracellular matrix. BrdU positive cells (cells indicated by arrows) were detected 1 day, 8, and 14 weeks after labeling with BrdU. Bar=25 µm. The bar graph on the right shows the percentage of BrdU-positive cells 1 day and 14 weeks after labeling with BrdU. The results shown are mean±SEM of 3 mice. The symbol * indicates a p value <0.0003 for cells 1 day vs. 14 weeks after labeling. FIG. 5B shows that BGN and FMOD are highly expressed in tendon. Tendons from $BGN^{-/}$o/$FMOD^{-/-}$ mice were used as negative control. Bar=25 µm. FIG. 5C illustrates the gross appearance of impaired tendon formation in a 4 month-old $BGN^{-/0}/FMOD^{-/-}$ mice. The patellar tendon (white bright tissue) was more translucent in $BGN^{-/0}/FMOD^{-/-}$ mice compared to WT mice. FIG. 5D shows H&E stained sagittal sections taken from the middle of patellar tendons from a 6 day-old WT and $BGN^{-/0}/FMOD^{-/-}$ mice. Collagen fibers were visualized under polarized light. Arrows indicate the gaps between the collagen fibrils. Bar=50 µm. The cell density was the average of two 2500 mm² areas on each of 3 separate sagittal sections of patellar tendon. The thickness of tendon was the average width of 3 separate sagittal sections of patellar tendon. The symbol * indicates a p value of <0.002 $BGN^{-/0}/FMOD^{-/-}$ vs. WT. FIG. 5E shows increased colony-forming efficiency of TSPCs in the absence of BGN and FMOD. The results shown are mean±SEM of 3 flasks. The symbol * means that the p value is <0.00002 for $BGN^{-/0}/FMOD^{-/-}$ vs. WT. FIG. 5F shows increased proliferation of TSPCs in the absence of BGN and FMOD. The proliferation was determined by BrdU labeling. Bar=100 µm. Data are the mean±SEM of 6-8 fields. The symbol * indicates that the p value <0.03 for $BGN^{-/0}/FMOD^{-/-}$ vs. WT. FIG. 5G illustrates the results of RT-PCR, showing the decreased expression of scleraxis in the absence of BGN and FMOD. Gapdh was used as loading control. The expression intensity was determined by densitometric analysis. FIG. 5H illustrates the decreased expression of type I collagen (Col I) in the absence of BGN and FMOD, as detected by immunocytochemistry. Bar=50 µm.

FIG. 6A shows MicroCT images of knees of 2 and 5 month-old $BGN^{-/0}/FMOD^{-/-}$ mice. As shown, patellae (arrows) and ectopic ossicles (asterisks) formed in tendon. FIG. 6B Immunocytochemistry showed the expression Type II collagen and aggrecan by TSPCs from WT and BGN$^{-/0}$/FMOD$^{-/-}$ mice. Bar=50 μm. FIG. 6C shows that TSPCs from BGN$^{-/0}$/FMOD$^{-/-}$ mice form bone after in vivo transplantation. H&E stained sections showed the formation of bone (b) and tendon-like tissue (arrows). Bar=100 μm. FIG. 6D shows that BMP2 activated TSPCs through the SMAD1/5/8 pathway. Western blot analysis showed that BMP2 induced phosphorylation of SMAD1/5/8 in TSPCs in 30 minutes. The expression of SMAD1 was down-regulated and Runx2/Cbfal was up-regulated after TSPCs and BMSCs were cultured in osteogenic induction medium in the presence of BMP2 for 10 days. Hsp90 was used as a loading control. FIG. 6E shows that BMP2 increased osteogenesis in vitro. Alkaline phosphatase activity and Ca$^{2+}$ accumulation were determined after TSPC and BMSCs were cultured in the absence and presence of 100 ng/ml BMP2 for 3 days or 3 weeks, respectively. Data are mean±SEM (n=3). The symbol * indicates that the p value is <0.0001 with vs. without BMP2. FIG. 6F shows BMP2 increased bone formation in vivo. TSPCs and BMSCs were cultured in osteogenic-induction medium for 2 weeks in the absence or presence of 100 ng/ml BMP2 and then transplanted with HA/TCP subcutaneously into immunocompromised mice. H&E staining showed that bone (b) and bone marrow (m) formed after 8 weeks. Bar=200 μm. FIG. 6G illustrates that western blot analysis showed that BMP2-induced phosphorylation of SMAD1/5/8 in TSPCs was increased in BGN$^{-/0}$/FMOD$^{-/-}$ TSPCs. Hsp90 was used as a loading control. The expression intensity was determined by densitometric analysis. FIG. 6H shows increased nuclear localization of P-SMAD1/5/8/ in BGN$^{-/0}$/FMOD$^{-/-}$ TSPCs with and without the treatment of BMP2 for 30 minutes, as detected by immunocytochemistry staining. Bar=50 μm. FIG. 6I shows that BMP2-induced transcriptional activity was increased in BGN$^{-/0}$/FMOD$^{-/-}$ TSPCs, as determined with a reporter plasmid expressing a BMP responsive luciferase construct (pID-lux). pGL3 was used as control vector. Data are mean±SEM (n=3). The symbol * indicates that the p value is <0.02 for BGN$^{-/0}$/FMOD$^{-/-}$ vs. WT.

FIG. 7A shows X-ray images of patellas from wild type and BGN$^{-/0}$/FMOD$^{-/-}$ mice, illustrating ectopic ossification in the tendons from wild type and mutant mice subject to treadmill running. The ectopic ossification comes from tendon stem cells that have formed bones instead of tendon due to overactive bone morphogenic (BMP) signaling. FIG. 7B graphically illustrates the area of ectopic ossification. X-rays were scanned and areas of ectopic ossification were determined using NIH image software. Normal (wild type/WT) and BGN/FMOD (DKO) mice were subject to mild treadmill running 3 days a week for one month. M=males and F=females, S=static (not running) and E=exercise (treadmill running). The wild type males and females did not show signs of ectopic ossification with or without exercise. Males were more prone to ectopic ossification than females and benefited more from the exercise regime. These data show that tendon stem cells are sensitive to biomechanical forces applied to the compromised extracellular matrix.

DETAILED DESCRIPTION OF THE INVENTION

Figure 1A:
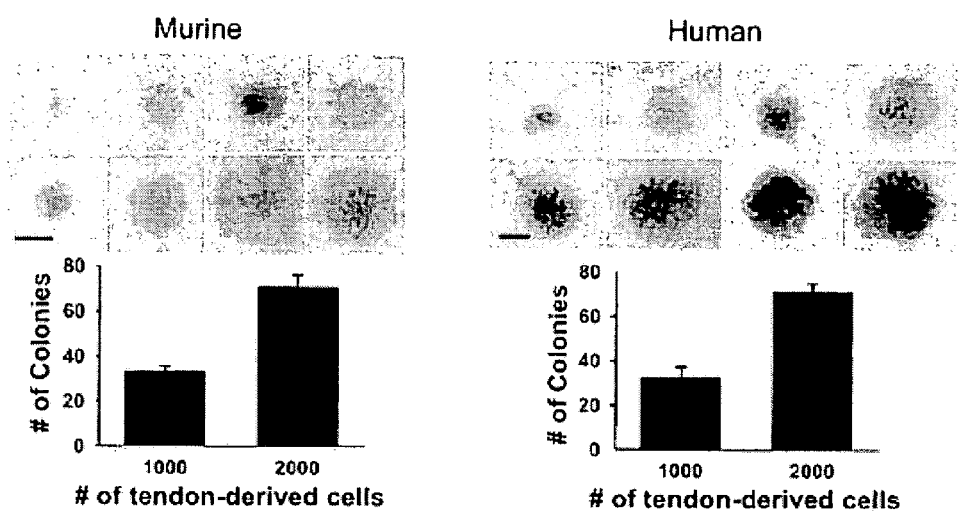
FIGS. 1A-1G illustrate the isolation and characterization of tendon stem/progenitor cells (TSPCs).

The invention involves tendon stem cells useful for treatment, repair and replacement of injured and/or diseased elastic and bone tissues, including skin, tendons, ligaments and bone.

Definitions

The following terms are defined herein as follows.

"Adipogenic" or "adipogenesis" refers to the development or generation of adipose, fat cells or fat cell containing tissues.

The term "carrier" refers to a vehicle with which a stem cell can be mixed prior to being implanted into an organism. Examples of carriers include, but are not limited to, saline solution, buffered saline solution, gelatin, polyvinyl sponges, collagen matrices, and hydroxyapatite/tricalcium phosphate ceramics. Carriers can be prepared in numerous forms. For example, carriers can be liquid, semi-solid or solid. Carriers can be formed into blocks, powders, strips, and the like. Carriers are known in the art and have been described (Krebsbach et al., *Transplantation*, 63:1059 (1997)). One example, of a carrier is a water-insoluble, off-white, nonelastic, porous, pliable product prepared from purified pork skin gelatin granules and water (commercially available as GELFOAM®). GELFOAM® is available as a sterile powder, which is a fine, dry, heat-sterilized light powder prepared by milling absorbable gelatin sponge, or a sterile sponge that may be cut without fraying. GELFOAM® can be administered by injection or other means and is able to absorb and hold within its interstices, many times its weight of cells, blood and fluids. Another suitable carrier is a solubilized basement membrane preparation extracted from EHS mouse sarcoma, a tumor rich in extracellular matrix proteins. This solubilized basement membrane preparation is commercially available from BD Biosciences as MATRIGEL®. Major components of this solubilized basement membrane preparation include laminin, collagen IV, heparin sulfate proteoglycans, and entactin. At room temperature, MATRIGEL® polymerizes to produce biologically active matrix material resembling the mammalian cellular basement membrane. Cells often behave as they do in vivo when cultured on or in MATRIGEL®. It may provide a physiologically relevant environment for multiplication and/or differentiation of stem cells.

"Chondrogenic" or "chondrogenesis" refers to the development or generation of tendon, ligament, and/or cartilage.

"Co-administer" can include simultaneous and/or sequential administration of two or more agents.

"Cytokines" refers to cellular factors that induce or enhance cellular movement, such as homing of TSPCs or other stem cells, progenitor cells, or differentiated cells. Cytokines may also stimulate such cells to divide.

"Differentiation factors" refers to cellular factors, including growth factors or other factors that induce lineage commitment.

An "effective amount" generally means an amount which provides the desired effect. For example, an effective dose is an amount sufficient to effect a beneficial or desired result. The dose could be administered in one or more administrations and can include any preselected amount of cells. The precise determination of what would be considered an effective dose may be based on factors individual to each subject, including size, age, injury (e.g., defect), or disease (e.g., defect) being treated and amount of time since the injury occurred or the disease began. One skilled in the art, particularly a physician, would be able to determine the number of cells that would constitute an effective dose. Doses can vary depending on the mode of administration, e.g., local or systemic; free or encapsulated. The effect can be engraftment or other clinical endpoints, such as reversal or treatment of tendon injury, disease, or problems. Other effects can include providing mature cells, recruiting endogenous cells, and/or effecting osteogenic, adipogenic, or chondrogenic progenitors.

"Engraft" or "engraftment" refers to the process of cellular contact and incorporation into an existing tissue or site of interest.

An "enriched population" means a relative increase in numbers of TSPC relative to one or more non-TSPC cell types in vivo or in cultures, including primary cultures, of different levels of purity. The cells can also be purified to varying degrees.

"Enthesis" refers to the junction between tendon and bone, and the structures that form at this junction.

"Expansion" refers to the propagation of cells without differentiation.

"Express" or "expression" refers to RNA and/or protein expression.

"Immunologic tolerance" refers to the survival in amount and/or length of time of foreign (e.g., allogeneic or xenogeneic) tissues, organs or cells in recipient subjects. This survival is often a result of the inhibition of a graft recipient's ability to mount an immune response that would otherwise occur in response to the introduction of foreign cells. Immune tolerance can encompass durable immunosuppression of days, weeks, months, or years.

The term "isolated" means that a cell of the invention is not in the state found in nature. For example, the cell is sufficiently free of contaminants or other cell types with which a cell of the invention is naturally found. The term isolated does not require a cell of the invention to be free of all contaminants.

"Multipotent," with respect to TSPC, refers to the ability to give rise to cell types of more than one differentiated lineage. TSPCs can give rise to osteogenesis, adipogenesis, chondrogenesis, or any combination thereof in a mammal.

"Osteogenic" or "osteogenesis" means the development or generation of bony tissue(s).

"Persistence" refers to the ability of cells to resist rejection and remain or increase in number over time (e.g., days, weeks, months, years) in vivo. Thus, by persisting, TSPCs or progeny differentiated therefrom can populate tissues or remain in vivo.

"Progenitor cells" are cells produced during differentiation of a stem cell that have some, but not all, of the characteristics of their terminally-differentiated progeny. Defined progenitor cells such as "osteogenic, adipogenic, or chondrogenic progenitor cells," are committed to a lineage, but not to a specific or terminally-differentiated cell type. The term "progenitor" as used in the acronym "TSPC" does not limit these cells to a particular lineage.

"Self-renewal" refers to the ability to produce replicate cells having differentiation potential that is identical to those from which they arose.

"Sharpey's fibers" are a matrix of connective tissue consisting of bundles of strong collagenous fibers connecting periosteum to bone. Sharpey's fibers are part of the outer fibrous layer of periosteum and enter into the outer circumferential and interstitial lamellae of bone tissue. The periosteum is a thin layer of dense, irregular connective tissue membrane that covers the outer surface of a bone in all places except at joints.

A "subject" is a vertebrate, preferably a mammal, more preferably a human. Mammals include, but are not limited to, humans, farm animals, sport animals, and pets. Included in the terms "animals" or "pets" are, but not limited to, dogs, cats, horses, rabbits, mice, rats, sheep, goats, cows, and birds.

"Tendons" are like ligaments in being tough, flexible cords, however, tendons differ from ligaments in that tendons extend from muscle to bone, whereas ligaments extend from bone to bone, for example, in a joint.

"TSPC" is an acronym for a "tendon stem/progenitor cell." The term "tendon stem cell" is used interchangeably with TSPC and tendon stem/progenitor cell. This term refers to non-embryonic stem (non-ES), non-germ stem cell (a non-embryonic somatic cell) that is capable of self-renewal and that can give rise to several cell types. For example, TSPCs can give rise to osteogenic and adipogenic cells. In general, TSPCs exhibit cell surface expression of CD44. Human TSPCs expressed Stro-1, CD146 (Muc18) 26327, CD 90, and CD44, but not CD18. However, TSPCs did not express hematopoietic cell markers, CD34, CD45 and c-kit or the endothelial cell marker, CD106. TSPCs can be derived from tendon tissues, for example, from the extracellular matrix of tendon tissues.

TSPCs injected into a mammal can engraft into and within mammalian tissues. For example, TSPCs can form tendons in vivo and these tendons can attach to bone. The TSPCs are also self-renewing. As such, they can repopulate tendons, ligaments, cartilage, or bone tissues, either in a self-renewing state or in a differentiated state. They have the capacity to replace cell types that have been damaged (due to disease (e.g., defect) or injury (e.g., defect)), died, or otherwise have an abnormal function (e.g., defect) because of genetic or acquired disease. Or, as discussed below, they may contribute to the preservation of healthy cells or production of new cells in a tissue.

As used herein, "treat," "treating" or "treatment" includes treating, reversing, preventing, ameliorating, or inhibiting an injury or disease-related condition (defect) or a symptom of an injury or disease-related condition (defect).

The terms "comprises", "comprising", and the like can have the meaning ascribed to them in U.S. Patent Law and can mean "includes", "including" and the like. As used herein, "including" or "includes" or the like means including, without limitation.

Tendon Stem Cells

According to the invention, non-embryonic (e.g., adult) tendon contains a population of stem cells. This was demonstrated by showing the cells were clonogenic, multipotent, and highly regenerative (e.g., over 20 population doublings in some experiments) both in vitro and in vivo. The tendon stem cells of the invention have the capacity to be induced to differentiate in vitro, ex vivo, or in vivo. The tendon stem cells can form tendon structures that can not only repopulate injured tendon tissues, but also can attach to bone in vivo and form enthesis-like structures.

Tendon stem cells of the invention can express higher levels of tendon-related factors, such as scleraxis, tenomodulin, and tenascin C, than stem or stromal cells isolated from bone marrow. Moreover, tendon stem cells generally do not express substantial amounts of CD18, a bone marrow stem cell marker.

The tendon stem cells of the invention can differentiate to tendon, ligament, cartilage (chondrocyte), and osteoblast cell types. The cells of the invention include clonal or nonclonal populations of the tendon stem cells, including populations of tendon cells enriched to various degrees.

Thus, the tendon stem cells can be used for tendon tissue repair and for repair of the tendon-bone junction. Using animal models deficient in two major components of tendon, biglycan, and fibromodulin, the inventors provide data showing that the fate of the tendon stem cell can be controlled by these extracellular matrix proteoglycans. Thus, the tendon stem cells can be cultivated and maintained and stimulated to form tendon in vivo. In some embodiments, the stem cells may be cultured with additional factors such as small proteoglycans (e.g., biglycan and fibromodulin) and/or collagen which protect the stem cells and can guide the differentiation of the stem cells. In other embodiments, the proteoglycans are not needed because the stem cells produce their own proteoglycans. Another factor that may be introduced into the culture medium is Bone Morphogenetic Protein 2 (BMP2), which can stimulate formation of bone-producing cells.

Tendon stem cells of the invention can be isolated from tendon tissues, particularly the extracellular matrix of tendon tissues. Further information on isolating, culturing, and using the tendon stem cells is provided below.

Tendon Development

The tendon is a connective tissue that connects muscle to bone and serves to transmit force. Tendons generally consist of highly aligned collagen fibrils organized as fibers. Fibroblasts are also present in tendon tissues. The fibers and tendon fibroblasts are organized into fascicles, and the fascicles are bound together by connective tissue sheaths to form a tendon.

The mechanical integrity and function of the tendon is dependent on a regulated progression of developmental and/or repair steps. In general, these steps involve collagen fibrillogenesis and matrix assembly. Collagen fibrillogenesis results in the assembly of mature collagen fibrils with a tissue-specific structure and function. There are at least three distinct steps in fibrillogenesis.

In the first step, collagen molecules assemble extracellularly in close association with the fibroblast surface to form immature fibril intermediates. This step can be influenced at a number of points, including during packaging for secretion, vectorial secretion into the extracellular space, procollagen processing, heterotypic collagen interactions, and other molecular interactions. Such factors may influence the nucleation and growth of the fibril intermediate.

In a second step, linear fibril growth, the preformed fibril intermediates assemble end-to-end to form longer fibrils that begin to resemble mature, mechanically functional fibrils.

In the third step, lateral fibril growth, the fibrils associate laterally to generate large diameter fibrils. This lateral growth step, coupled with linear growth, generates the long, large diameter fibrils characteristic of the mature tendon.

Tendon fibrils are heteropolymeric structures assembled from two or more different fibril-forming collagens interacting with fibril-associated collagens as well as fibril-associated proteoglycans. The tendon is composed of type I collagen with quantitatively minor amounts of types III and V collagen. The D-periodic fibrils are predominantly type I collagen with varying amounts of collagen type V and III3. Collagen types XII and XIV have different expression patterns during tendon development. These collagens are found on the surface of striated collagen fibrils. Because of their fibril-associated nature, these macromolecules may be involved both in the regulation of fibril formation and in modifying the interaction(s) among fibrils required for the assembly of tissue-specific extracellular matrices. In addition, members of the leucine-rich repeat family of proteoglycans/glycoproteins are associated with tendon fibrils. Interactions between collagen fibrils and members of this family of proteoglycans/glycoproteins have been implicated in the regulation of fibrillogenesis. See, Zhang et al., *J. Musculoskelet. Neuronal Interact.*, 5(1):5-21 (2005).

Interactions between the fibrils and their surrounding molecules also play a significant role in tendon mechanics. In particular, the development of the mature mechanical properties of tendons is dependent on the assembly of a tendon-specific extracellular matrix. This assembly process progresses through multiple steps producing the final mature structure where tendon fibroblasts and collagen fibrils (organized as fibers) are integrated into a functional tissue. Id.

According to the invention, the present stem cells can orchestrate each of the steps involved in tendon development and repair described above.

Biglycan and Fibromodulin

According to the invention, biglycan and fibromodulin can protect the present stem cells and can also modulate the differentiation of the present tendon stem cells. In particular, biglycan and fibromodulin may help to maintain tendon stem cells for expansion so that an expanded population of essentially undifferentiated stem cells is available for use in tissue engineering. For example, biglycan and fibromodulin can inhibit ectopic ossification of the tendon tissue. In other embodiments, biglycan and fibromodulin can guide the differentiation of tendon stem cells, for example, away from bone formation and towards tendon formation.

Biglycan is a member of the leucine-rich repeat (LRR) protein family, and is composed of a 38 kDa core protein that is substituted with two glycosaminoglycan chains on N-terminal Ser-Gly sites. The core protein contains ten leucine-rich repeats flanked by disulphide bond stabilized loops on both sides. It contains additional sites for glycosylation (N-linked glycosylation sites) within the leucine-rich repeats. The quality of the glycosaminoglycans varies both with regard to length and composition. The backbone of the glycosaminoglycan chain is composed of repeating disaccharide units of N-acetylgalactosamine and glucuronic acid, the latter often being converted into iduronic acid through epimerization at carbon 5. As the chains are elongated, they are modified by sulphation resulting in chondroitin sulfate and dermatan sulfate, respectively. The degree of epimerization and sulphation varies between tissues. An isoform of biglycan with a single glycosaminoglycan substitution has been found.

Biglycan interacts with collagen VI and the complement component C1q. Conflicting data exists as to whether biglycan interacts with fibrillar collagens or not. Thus, the protein binds to wells coated with the collagen but appears not to precipitate with collagen fibers. Biglycan is also a zinc-binding protein. The interaction with the collagen molecule is not modulated by the GAG chains. Biglycan also interacts with transforming growth factor-β (TGF-β). Biglycan may also efficiently accelerate and organize collagen VI assembly into structured networks. This property requires the intact molecule with its two glycosaminoglycan chains. The core protein, while still binding to collagen VI, does not catalyze this organization. It has also been shown that biglycan bound to the N-terminal globular domain of collagen type VI at the same time can bind to matrilin-1, 2, or 3. The latter molecule can in turn reach the collagen molecules, collagen fibers, as well as aggrecan.

Sequences for biglycan from various species are available in the National Center for Biotechnology Information (NCBI) database (http://www.ncbi.nlm.nih.gov/). For example, a human biglycan sequence is available as accession number AAH04244 (gi: 13279002). This sequence is provided below for easy reference (SEQ ID NO:1).

```
  1   MWPLWRLVSL  LALSQALPFE  QRGFWDFTLD  DGPFMMNDEE
 41   ASGADTSGVL  DPDSVTPTYS  AMCPFGCHCH  LRVVQCSDLG
 81   LKSVPKEISP  DTTLLDLQNN  DISELRKDDF  KGLQHLYALV
```

```
121  LVNNKISKIH EKAFSPLRKL QKLYISKNHL VEIPPNLPSS
161  LVELRIHDNR IRKVPKGVFS GLRNMNCIEM GGNPLENSGF
201  EPGAFDGLKL NYLRISEAKL TGIPKDLPET LNELHLDHNK
241  IQAIELEDLL RYSKLYRLGL GHNQIRMIEN GSLSFLPTLR
281  ELHLDNNKLA RVPSGLPDLK LLQVVYLHSN NITKVGVNDF
321  CPMGFGVKRA YYNGISLFNN PVPYWEVQPA TFRCVTDRLA
361  IQFGNYKK
```

A nucleotide sequence for the above biglycan polypeptide is also available in the NCBI database as accession number BC004244 (gi: 13279001). This nucleotide sequence for human biglycan is provided below for easy reference (SEQ ID NO:2).

```
   1  AATTCGGCAT GAGGGGAGTG AGTAGCTGCT TTCGGTCCGC
  41  CGGACACACC GGACAGATAG ACGTGCGGAC GGCCCACCAC
  81  CCCAGCCCTC CAACTAGTCA GCCTGCGCCT GGCGCCTCCC
 121  CTCTCCAGGT CCATCCGCCA TGTGGCCCCT GTGGCGCCTC
 161  GTGTCTCTGC TGGCCCTGAG CCAGGCCCTG CCCTTTGAGC
 201  AGAGAGGCTT CTGGGACTTC ACCCTGGACG ATGGGCCATT
 241  CATGATGAAC GATGAGGAAG CTTCGGGCGC TGACACCTCA
 281  GGCGTCCTGG ACCCGGACTC TGTCACACCC ACCTACAGCG
 321  CCATGTGTCC TTTCGGCTGC CACTGCCACC TGCGGGTGGT
 361  TCAGTGCTCC GACCTGGGTC TGAAGTCTGT GCCCAAAGAG
 401  ATCTCCCCTG ACACCACGCT GCTGGACCTG CAGAACAACG
 441  ACATCTCCGA GCTCCGCAAG GATGACTTCA AGGGTCTCCA
 481  GCACCTCTAC GCCCTCGTCC TGGTGAACAA CAAGATCTCC
 521  AAGATCCATG AGAAGGCCTT CAGCCCACTG CGGAAGCTGC
 561  AGAAGCTCTA CATCTCCAAG AACCACCTGG TGGAGATCCC
 601  GCCCAACCTA CCCAGCTCCC TGGTGGAGCT CCGCATCCAC
 641  GACAACCGCA TCCGCAAGGT GCCCAAGGGA GTGTTCAGCG
 681  GGCTCCGGAA CATGAACTGC ATCGAGATGG GCGGGAACCC
 721  ACTGGAGAAC AGTGGCTTTG AACCTGGAGC CTTCGATGGC
 761  CTGAAGCTCA ACTACCTGCG CATCTCAGAG GCCAAGCTGA
 801  CTGGCATCCC CAAAGACCTC CCTGAGACCC TGAATGAACT
 841  CCACCTAGAC CACAACAAAA TCCAGGCCAT CGAACTGGAG
 881  GACCTGCTTC GCTACTCCAA GCTGTACAGG CTGGGCCTAG
 921  GCCACAACCA GATCAGGATG ATCGAGAACG GGAGCCTGAG
 961  CTTCCTGCCC ACCCTCCGGG AGCTCCACTT GGACAACAAC
1001  AAGTTGGCCA GGGTGCCCTC AGGGCTCCCA GACCTCAAGC
1041  TCCTCCAGGT GGTCTATCTG CACTCCAACA ACATCACCAA
1081  AGTGGGTGTC AACGACTTCT GTCCCATGGG CTTCGGGGTG
1121  AAGCGGGCCT ACTACAACGG CATCAGCCTC TTCAACAACC
1161  CCGTGCCCTA CTGGGAGGTG CAGCCGGCCA CTTTCCGCTG
1201  CGTCACTGAC CGCCTGGCCA TCCAGTTTGG CAACTACAAA
1241  AAGTAGAGGC AGCTGCAGCC ACCGCGGGGC CTCAGTGGGG
1281  GTCTCTGGGG AACACAGCCA GACATCCTGA TGGGGAGGCA
1321  GAGCCAGGAA GCTAAGCCAG GGCCCAGCTG CGTCCAACCC
1361  AGCCCCCCAC CTCGGGTCCC TGACCCCAGC TCGATGCCCC
1401  ATCACCGCCT CTCCCTGGCT CCCAAGGGTG CAGGTGGGCG
1441  CAAGGCCCGG CCCCCATCAC ATGTTCCCTT GGCCTCAGAG
1481  CTGCCCCTGC TCTCCCACCA CAGCCACCCA GAGGCACCCC
1521  ATGAAGCTTT TTTCTCGTTC ACTCCCAAAC CCAAGTGTCC
1561  AAGGCTCCAG TCCTAGGAGA ACAGTCCCTG GGTCAGCAGC
1601  CAGGAGGCGG TCCATAAGAA TGGGGACAGT GGGCTCTGCC
1641  AGGGCTGCCG CACCTGTCCA GACACACATG TTCTGTTCCT
1681  CCTCCTCATG CATTTCCAGC CTTTCAACCC TCCCCGACTC
1721  TGCGGCTCCC CTCAGCCCCC TTGCAAGTTC ATGGCCTGTC
1761  CCTCCCAGAC CCCTGCTCCA CTGGCCCTTC GACCAGTCCT
1801  CCCTTCTGTT CTCTCTTTCC CCGTCCTTCC TCTCTCTCTC
1841  TCTCTCTCTC TCTCTCTCTT TCTGTGTGTG TGTGTGTGTG
1881  TGTGTGTGTG TGTGTGTGTG TCTTGTGCTT CCTCAGACCT
1921  TTCTCGCTTC TGAGCTTGGT GGCCTGTTCC CTCCATCTCT
1961  CCGAACCTGG CTTCGCCTGT CCCTTTCACT CCACACCCTC
2001  TGGCCTTCTG CCTTGAGCTG GGACTGCTTT CTGTCTGTCC
2041  GGCCTGCACC CAGCCCCTGC CCACAAAACC CCAGGGACAG
2081  CGGTCTCCCC AGCCTGCCCT GCTCAGGCCT TGCCCCCAAA
2121  CCTGTACTGT CCCGGAGGAG GTTGGGAGGT GGAGGCCCAG
2161  CATCCCGCGC AGATGACACC ATCAACCGCC AGAGTCCCAG
2201  ACACCGGTTT TCCTAGAAGC CCCTCACCCC CACTGGCCCA
2241  CTGGTGGCTA GGTCTCCCCT TATCCTTCTG GTCCAGCGCA
2281  AGGAGGGGCT GCTTCTGAGG TCGGTGGCTG TCTTTCCATT
2321  AAAGAAACAC CGTGCAACGT GAAAAAAAAA AAAAAAAAAA
2361  AAAAAAAAAA AAAAAAAAAA AAAAAAAAAA AAAAAAAAAA
2401  AAAAAAAAAA AAAACCCTCG GG
```

Fibromodulin (FMOD) is an abundant member of the leucine-rich repeat protein family, first described as a 59 kDa collagen binding protein. This protein has sequence homology with PRELP, lumican (LMN), keratocan, and osteoadherin. Fibromodulin protein contains keratan sulfate with four potential substitution sites, all present in the leucine-rich region. These sulfated N-linked oligosaccharides are short in length (on average 9 disaccharide units) and are similar in structure in bovine, equine, and human fibromodulin. Tyrosine sulfation sites have also been identified in the N-terminal part of the molecule between Gln19 and Pro70 with up to nine tyrosine residues modified by sulfate.

Fibromodulin interacts with both types of collagens I and II. Fibromodulin is present on collagen fibers (gap region) in cartilage, with a higher surface density on fibers in the superficial region and present in increased amounts in the interterritorial matrix of all layers. FMOD-null mice have abnormally thin collagen fibrils in tendon tissues. Binding of fibromodulin to type XII collagen and interaction with growth factor TGF-β have also been reported. A single high affinity binding site and one of lower affinity is present on the core fibromodulin protein. Binding of TGF-β to fibromodulin and other small proteoglycans may serve as a reservoir of this growth factor within the matrix.

Sequences for fibromodulin from various species are available in the NCBI database (http://www.ncbi.nlm.nih.gov/). For example, a human fibromodulin sequence is available as accession number CAA53233 (gi: 453157). This sequence is provided below for easy reference (SEQ ID NO:3).

```
  1  MQWASLLLLA GLFSLSQAQY EDDPHWWFHY LRSQQSTYYD
 41  PYDPYPYETY EPYPYGVDEG PAYTYGSPSP PDPRDCPQEC
 81  DCPPNFLTAM YCDNRNLKYL PFVPSRMKYV YFQNNQITSI
121  QEGVFDNATG LLWIALHGNQ ITSDKVGRKV FSKLRHLERL
161  YLDHNNLTRM PGPLPRSLRE LHLDHNQISR VPNNALEGLE
201  NLTALYLQHD EIQEVGSSMR GLRSLILLDL SYNHLRKVPD
241  GLPSALEQLY MEHNNVYTVP DSYFRGAPKL LYVRLSHNSL
281  TNNGLASNTF NSSSLLELDL SYNQLQKIPP VNTNLENLYL
321  QGNRINEFSI SSFCTVVDVV NFSKLQVVRL DGNEIKRSAM
361  PADAPLCLRL ASLIEI
```

A nucleotide sequence for the above fibromodulin polypeptide is also available in the NCBI database as accession number X75546 (gi: 453156). This nucleotide sequence for human fibromodulin is provided below for easy reference (SEQ ID NO:4).

```
  1  CGGAATTCAA GAAACACAAA ATGCAGTGGG CGTCCCTCCT
 41  GCTGCTGGCA GGGCTCTTCT CCCTCTCCCA GGCCCAGTAT
 81  GAAGATGACC CTCATTGGTG GTTCCACTAC CTCCGCAGCC
121  AGCAGTCCAC CTACTACGAT CCCTATGACC CTTACCCGTA
161  TGAGACCTAC GAGCCTTACC CCTATGGGGT GGATGAAGGG
201  CCAGCCTACA CCTACGGCTC TCCATCCCCT CCAGATCCCC
241  GCGACTGCCC CCAGGAATGC GACTGCCCAC CCAACTTCCT
281  CACGGCCATG TACTGTGACA ATCGCAACCT CAAGTACCTG
321  CCCTTCGTTC CCTCCCGCAT GAAGTATGTG TACTTCCAGA
361  ACAACCAGAT CACCTCCATC CAGGAAGGCG TCTTTGACAA
401  TGCCACAGGG CTGCTCTGGA TTGCTCTCCA CGGCAACCAG
441  ATCACCAGTG ATAAGGTGGG CAGGAAGGTC TTCTCCAAGC
481  TGAGGCACCT GGAGAGGCTG TACCTGGACC ACAACAACCT
521  GACCCGGATG CCCGGTCCCC TGCCTCGATC CCTGAGAGAG
561  CTCCATCTCG ACCACAACCA GATCTCACGG GTCCCCAACA
601  ATGCTCTGGA GGGGCTGGAG AACCTCACGG CCTTGTACCT
641  CCAACACGAT GAGATCCAGG AAGTGGGCAG TTCCATGAGG
681  GGCCTCCGGT CACTGATCTT GCTGGACCTG AGTTATAACC
721  ACCTTCGGAA GGTGCCTGAT GGGCTGCCCT CAGCTCTTGA
761  GCAGCTGTAC ATGGAGCACA ACAATGTCTA CACCGTCCCC
801  GATAGCTACT TCCGGGGGGC GCCCAAGCTG CTGTATGTGC
841  GGCTGTCCCA CAACAGTCTA ACCAACAATG GCCTGGCCTC
881  CAACACCTTC AATTCCAGCA GCCTCCTTGA GCTAGACCTC
921  TCCTACAACC AGCTGCAGAA GATCCCCCCA GTCAACACCA
961  ACCTGGAGAA CCTCTACCTC CAAGGCAATA GGATCAATGA
1001 GTTCTCCATC AGCAGCTTCT GCACCGTGGT GGACGTCGTG
1041 AACTTCTCCA AGCTGCAGGT CGTGCGCCTG GACGGGAACG
1081 AGATCAAGCG CAGCGCCATG CCTGCCGACG CGCCCCTCTG
1121 CCTGCGCCTT GCCAGCCTCA TCGAGATCTG AGCAGCCCTG
1161 GCACCGGGTA CTGGGCGGAG AGCCCCCGTG GCATTTGGCT
1201 TGATGGTTTG GTTTGGCTTA TGGAAGATCT GGGACAGACC
1241 GTGTGAC
```

Bone Morphogenetic Protein 2 (BMP2)

According to the invention, bone and/or bone-producing cells can be generated by exposing the tendon stem cells of the invention to bone morphogenetic protein 2 (BMP2). BMP2 belongs to the TGFβ superfamily. The BMP2 protein is a disulfide-linked homodimer, and induces bone and cartilage formation.

BMP2 is available, for example, from Wyeth Pharmaceuticals. Sequences for BMP2 from various species are available in the NCBI database (http://www.ncbi.nlm.nih.gov/). For example, a human BMP2 preprotein sequence is available as accession number NP_001191 (gi: 4557369). This sequence is provided below for easy reference (SEQ ID NO:5).

```
  1  MVAGTRCLLA LLLPQVLLGG AAGLVPELGR RKFAAASSGR
 41  PSSQPSDEVL SEFELRLLSM FGLKQRPTPS RDAVVPPYML
 81  DLYRRHSGQP GSPAPDHRLE RAASRANTVR SFHHEESLEE
121  LPETSGKTTR RFFFNLSSIP TEEFITSAEL QVFREQMQDA
161  LGNNSSFHHR INIYEIIKPA TANSKFPVTR LLDTRLVNQN
201  ASRWESFDVT PAVMRWTAQG HANHGFVVEV AHLEEKQGVS
241  KRHVRISRSL HQDEHSWSQI RPLLVTFGHD GKGHPLHKRE
281  KRQAKHKQRK RLKSSCKRHP LYVDFSDVGW NDWIVAPPGY
321  HAFYCHGECP FPLADHLNST NHAIVQTLVN SVNSKIPKAC
361  CVPTELSAIS MLYLDENEKV VLKNYQDMVV EGCGCR
```

The first 23 amino acids of this protein are a signal peptide. Thus, without the signal peptide, the above BMP2 protein has the following proprotein sequence (SEQ ID NO:6).

```
  1  LVPELGR RKFAAASSGR
 41  PSSQPSDEVL SEFELRLLSM FGLKQRPTPS RDAVVPPYML
 81  DLYRRHSGQP GSPAPDHRLE RAASRANTVR SFHHEESLEE
```

-continued

```
121  LPETSGKTTR  RFFFNLSSIP  TEEFITSAEL  QVFREQMQDA

161  LGNNSSFHHR  INIYEIIKPA  TANSKFPVTR  LLDTRLVNQN

201  ASRWESFDVT  PAVMRWTAQG  HANHGFVVEV  AHLEEKQGVS

241  KRHVRISRSL  HQDEHSWSQI  RPLLVTFGHD  GKGHPLHKRE

281  KRQAKHKQRK  RLKSSCKRHP  LYVDFSDVGW  NDWIVAPPGY

321  HAFYCHGECP  FPLADHLNST  NHAIVQTLVN  SVNSKIPKAC

361  CVPTELSAIS  MLYLDENEKV  VLKNYQDMVV  EGCGCR
```

Amino acids 24-36 of the preproprotein (SEQ ID NO:3) are proprotein sequences. Thus, without the proprotein peptidyl sequences, the above BMP2 protein has the following mature protein sequence (SEQ ID NO:7).

```
  1  SSGR

41  PSSQPSDEVL  SEFELRLLSM  FGLKQRPTPS  RDAVVPPYML

81  DLYRRHSGQP  GSPAPDHRLE  RAASRANTVR  SFHHEESLEE

121  LPETSGKTTR  RFFFNLSSIP  TEEFITSAEL  QVFREQMQDA

161  LGNNSSFHHR  INIYEIIKPA  TANSKFPVTR  LLDTRLVNQN

201  ASRWESFDVT  PAVMRWTAQG  HANHGFVVEV  AHLEEKQGVS

241  KRHVRISRSL  HQDEHSWSQI  RPLLVTFGHD  GKGHPLHKRE

281  KRQAKHKQRK  RLKSSCKRHP  LYVDFSDVGW  NDWIVAPPGY

321  HAFYCHGECP  FPLADHLNST  NHAIVQTLVN  SVNSKIPKAC

361  CVPTELSAIS  MLYLDENEKV  VLKNYQDMVV  EGCGCR
```

Generating Tendon, Cartilage, and/or Bone

The invention provides a method to repair, replace, or produce elastic tissues such as tendon and/or ligament, as well as tissues such as cartilage, adipose, and/or bone tissue in vitro and/or in vivo.

One embodiment of the invention is a method of producing elastic tissues (e.g. tendon and/or ligament), cartilage, adipose, and/or bone tissue in vivo. This method involves administering or implanting a stem cell of the invention into a mammal such that the stem cell is able to multiply and differentiate into elastic tissue (e.g., tendon and/or ligament), cartilage, adipose, and/or bone-producing tissue in vivo. For example, these methods for producing elastic tissues, cartilage, adipose, and/or bone can involve administering or implanting the stem cell or a population of stem cells into the organism such that the desired product is formed. In some embodiments, the stem cell can be administered to the mammal and find its way to appropriate sites (e.g., injured/diseased tendons). For example, the stem cells may be administered into the bloodstream of the mammal. However, in many embodiments, the stem cell or population of stem cells is implanted at desired sites, for example, sites in need of elastic tissue, cartilage, adipose, or bone tissue repair. According to the invention, the environment into which the stem cell is implanted can influence the type of differentiated cells that form from the stem cell. Thus, for example, when implanted into an environment that includes extracellular matrix components from tendon tissues, the stem cells multiply and differentiate to form tendon structures (e.g., parallel arrangements of collagen fibers, formation of Sharpey's fibers, and attachments of tendon to bone). Methods to preserve, administer, and implant cells are described herein and are available in the art.

The stem cells may be expanded ex vivo prior to being implanted or administered into a mammal. In addition, a postnatal stem cell of the invention may be implanted in combination, or not in combination, with a carrier. Numerous carriers are known in the art and are available. Examples of a carrier that may be used in accordance with the invention are extracellular matrix components, hydroxyapatite/tricalcium phosphate, MATRIGEL® and/or GELFOAM®. Purified or impure extracellular matrix components can be used as carriers. Thus, the entirety of an isolated extracellular matrix can be employed, or a complex mixture of extracellular matrix components can be employed, or single components such as biglycan, fibromodulin and/or collagen (e.g., collagen I) can be used as carrier.

The stem cells of the invention can also be implanted or administered in combination with a drug, cytokine, or agent that can modulate the differentiation and/or growth of the stem cell. For example, the cells may be implanted with a cytokine, antibiotic, an antifungal, and the like. Numerous drugs are known in the art (Merck Index, 13th edition, Whitehouse Station, N.J., (2001)) and can be used with the compositions and stem cells of the invention.

One method for producing tendon, cartilage, adipose, and/or bone tissue in vitro involves culturing the tendon stem cells of the invention in a culture medium for a time and under conditions sufficient for generating a larger population of stem cells. Such a time can vary depending upon the numbers or quantity of stem cells desired. In general, the stem cells are cultured for about 3 days to about 45 days, or for about 4 days to about 40 days, or for about 5 days to about 35 days, or for about 5 days to about 30 days. The conditions can include culture conditions commonly used for culturing mammalian cells. In general, any available media for culturing mammalian cells, particularly primary mammalian cells, can be used. For example, the culture media can be any media used for culturing primary cells, chondrocytes, osteoblasts, adipocytes, and the like. In some embodiments, Dulbecco's Modified Eagle's Medium (DMEM) (GIBCO®) can be used. Such culture media can be supplemented with about 3% to about 30% fetal serum, e.g. fetal bovine serum. In some embodiments, the amount of fetal serum employed is about 5% to about 25% fetal serum. In other embodiments, the amount of serum employed is about 7% to about 20% fetal serum. In further embodiments, the amount of serum employed is about 8% to about 15% fetal serum. Some antibacterial and/or antimicrobial agents can also be present in the culture media, for example, penicillin and/or streptomycin and/or gentamicin.

In some embodiments, it is desirable to expand the stem cells while maintaining the stem cells in a relatively undifferentiated state. This is generally not a problem for the present tendon stem cells because the cells remain essentially undifferentiated without addition of any factors or agents to the culture medium. However, to protect and/or maintain the stem cells in an essentially undifferentiated state, the cells can be cultured in an effective amount of biglycan and/or fibromodulin.

In other embodiments, it is desirable to promote formation of specific differentiated cell types. For example, bone-producing cells can be generated in culture by exposing the tendon stem cells to an appropriate concentration of BMP2. This can be done while a population of stem cells is in culture, or the BMP2 can be combined with the cells and carrier used during administration and/or implantation. In further embodiments, extracellular matrix components such as biglycan and/or fibromodulin and/or collagen may promote formation of tendon cells.

The type of cell into which the postnatal stem cell differentiates is thought to depend upon the cellular environment into which the cell is implanted. For example, implantation of a stem cell of the invention into tendon tissue is thought to cause the cell to differentiate into a tendon cell. Alternatively, a postnatal stem cell of the invention can be cultured under inducing conditions to cause the postnatal stem cell to differentiate into a desired cell type. This culturing may be conducted prior to implantation of the differentiated or partially differentiated cell into an organism. For example, a postnatal stem cell of the invention may be subjected to mineralizing induction, induction with BMP2, neuronal induction, or adipocyte induction.

The stem cells of the invention can be implanted into an organism to treat, repair, or reduce the symptoms of numerous conditions and diseases. For example, a stem cell of the invention can be administered or implanted into a torn, injured, or diseased elastic tissue thereby promoting formation of healthy tissue with elastic properties (e.g., healthy tendon or cartilage). In another example, a stem cell of the invention may be implanted into sites of attachment between elastic tissue and bone to promote reattachment of the elastic tissue to bone. In another example, a stem cell of the invention may be implanted into the site of a physical injury to bone to reduce the severity of the injury or to promote healing of the injury. As described herein to promote healing of injuries to bone, the stem cells may be treated with bone morphogenetic protein 2 (BMP2). In another example, a postnatal stem cell of the invention may be implanted into an organism to create fat when needed. Such fat creation can be used to reduce or ameliorate serious disorders (lyodystrophies) where fat is lacking in different or in all parts of the body. These patients often experience severe problems related to energy metabolism which is highly dependent upon fat.

Any tendon can be treated and/or repaired using the present stem cells, compositions and methods. For example, tendon conditions and diseases that can be treated using the present invention include, but are not limited to, anterior cruciate ligament injuries and problems, tendonitis, tendon rupture, severed or torn tendon, Achille's tendonitis, torn or ruptured Achille's tendon, rotator cuff tendonitis, bursitis, retrocalcaneal bursitis, tenosynovitis, club foot (e.g., after corrective surgery), psoriatic arthritis, rheumatoid arthritis (often associated with tenosynovial proliferation), "jumpers knee" (where the tendon separates from the bone), or other tendon injuries that come from overuse or trauma and combinations thereof.

Torn or ruptured tendons, for example, Achilles' tendon rupture, can be treated and/or repaired using the stem cells and methods of the invention. Such an Achilles' tendon rupture is characterized by a popping feeling and then pain in the lower heel that makes it difficult to walk or run. The Achilles' tendon connects the two large muscles of the calf to the heel. The Achilles' tendon and these muscles work together and allow a person to point his or her toes, to stand on his or her toes, and to generate the power needed to push off with the foot when a person walks or runs. If overstretched, tendon can rupture. Ruptures can occur anywhere along the tendon, but for the Achille's tendon, ruptures are most common at the heel where the tendon also will be sensitive to the touch. The degree to which a person can use his or her foot and the degree of pain relate to whether the tendon is partially or completely ruptured. Similar conditions include Achilles' tendonitis or bursitis, which may result from inflammation and can occur when the tendon is overworked. However, unlike tendonitis and bursitis, which often improve with rest and the use of anti-inflammatory medications, prior to the invention a rupture of an Achille's tendon usually required surgical repair.

The identification of stem cells in tendon that have regenerative capacity shows they have the potential to be used to treat common injuries to tendon, including injuries where the tendon separates from the bone, or other tendon injuries that come from overuse or trauma. Currently there are no good cell based therapies to remedy tendon pathologies, which are common problem in orthopedics. The present discovery that tendon has stem cells is the first of its kind. Previous studies used bone marrow stromal cells to repair tendon but, as described herein, bone marrow stromal cells are different from tendon stem cells. The discovery of stem cells from tendon that possess regenerative capability opens new possibilities to treat damaged tendon tissue that is slow to repair after injury. Unlike other autologous grafts tissue such as bone, which can be harvested in large quantities from large bones such as the pelvis, autologous tendon for use as grafting material is not readily available. However, the ability to isolate cells from a small portion of tendon that can be expanded over multiple cell divisions and that subsequently form tendon tissue with capacity to integrate into bone offers a new strategy to improve the current means of tendon repair.

As also described herein, the stem cells in tendon are affected by the composition of the extracellular environment. In particular, a combination of the extracellular matrix proteoglycans biglycan and fibromodulin can be used to maintain tendon stem cells for expansion and for use in tissue engineering. The procedures used to isolate and use tendon stem cells for regeneration can be applied commercially. The animal model that is deficient in biglycan and fibromodulin additionally points to a role for these agents in inhibiting ectopic ossification of the tendon tissue. Biglycan and fibromodulin, therefore, can be used to inhibit ectopic bone formed during ankylosis or when tendons are subject to trauma and/or injury.

Also, according to the invention, these extracellular matrix components can be used to remedy other kinds of diseases and conditions involving pathological ectopic calcification. For example, such ectopic calcification occurs around artificial heart valves, atherosclerotic lesions, or in the rare inherited disease fibrodysplasia ossificans progressiva (FOP). This latter disease is caused by overactive BMP signaling and about 71% of FOP patients have jaw restriction by age 18 due to abnormal ossification of the ligaments. According to the invention, FOP can be treated and/or ameliorated by administration of biglycan and/or fibromodulin, either directly or by use of the present stem cells. For example, the stem cells of the invention may be transfected with nucleic acid constructs that allow the transfected cells to express a desired product (e.g., biglycan and/or fibromodulin). Accordingly, these transfected cells may be implanted into an organism prior to being differentiated such that the cells not only express biglycan and/or fibromodulin, but also repopulate the tendons (including the jaw tendons) of a patient with FOP.

Gene Therapy

The stem cells of the invention can also be genetically altered using a variety of techniques. Retroviral and other vectors for inserting foreign DNA into stem cells are available to those of skill in the art. Mochizuki et al., *J. Virol.*, 72:8873-8883 (1998); Robbins et al., *J. Virol.*, 71(12):9466-9474 (1997); Bierhuizen et al., *Blood*, 90(9):3304-3315 (1997); Douglas et al., *Hum. Gene Ther.*, 10(6):935-945 (1999); Douglas et al., *Nature Biotech.*, 17:470-475 (1999); Zhang et al., *Biochem. Biophys. Res. Commun.*, 227(3):707-711 (1996).

Thus, tendon stem cells or differentiated progeny derived therefrom can be genetically altered ex vivo, eliminating one of the most significant barriers for gene therapy. For example, a subject's tendon tissue is obtained and stem cells are isolated therefrom. The stem cells are then genetically altered to express one or more preselected gene products (e.g., cytokines, growth factors, and the like). The stem cells can then be screened or selected ex vivo to identify those cells which have been successfully altered, and these cells can be introduced into a subject or can be differentiated and introduced into a subject either locally or systemically. Alternately, stem cells can be differentiated and then the differentiated cells can be genetically altered prior to administration.

Cells isolated by the methods described herein, or their differentiated progeny, can be genetically modified by introducing DNA (e.g., including biglycan and/or fibromodulin DNA such as SEQ ID NO:2 and/or 4) or RNA into the cell by a variety of methods available to those of skill in the art: viral transfer (Mochizuki et al., *J. Virol.*, 72:8873-8883 (1998); Martin et al., *J. Virol.*, 73:6923-6929 (1999); Robbins et al., *J. Virol.*, 71(12):9466-9474 (1997); Salmons et al., *Hum. Gene Ther.*, 4:129-141 (1993); Sutton et al., *J. Virol.*, 72:5781-5788 (1998); Kafri et al., *J. Virol.*, 73:576-584 (1999); Dull et al., *J. Virol.*, 72:8463-8471 (1998), Davidson et al., *Nature Genetics*, 3:219-223 (1993); Wagner et al., *Proc. Natl. Acad. Sci. USA*, 89:6099-6103 (1992); Wold, *Adenovirus Methods and Protocols*, Human Methods in Molecular Medicine, Blackwell Science, Ltd. (1998); Molin et al., *J. Virol.*, 72:8358-8361 (1998); Douglas et al., *Hum. Gene Ther.*, 10(6):935-945 (1999); Douglas et al. *Nature Biotech.*, 17:470-475 (1999); Hofmann et al., *J. Virol.*, 73:6930-6936 (1999); Schwarzenberger et al., *J. Virol.*, 71:8563-8571 (1997), U.S. Pat. No. 5,843,723; Xiong et al., *Science*, 243:1188-1191 (1989); Bredenbeek et al., *J. Virol.*, 67:6439-6446 (1993); Frolov et al., *Proc. Natl. Acad. Sci. USA*, 93:11371-11377 (1996); Laquerre et al., *J. Virol.*, 72:9683-9697 (1998)); chemical transfer (e.g., calcium phosphate transfection and DEAE dextran transfection methods); membrane fusion transfer (Loeffler et al., *Methods in Enzymology*, 217:599-618 (1993); or physical transfer techniques (e.g., microinjection, microprojectile, electroporation, nucleofection or direct "naked" DNA transfer; J. Wolff in "Gene Therapeutics" (1994) at page 195; Johnston et al., *Genet. Eng. (NY)*, 15:225-236 (1993); Williams et al., *Proc. Natl. Acad. Sci. USA*, 88:2726-2730 (1991); Yang et al., *Proc. Natl. Acad. Sci. USA*, 87:9568-9572 (1990)).

Cells can be genetically altered by insertion of preselected isolated DNA, by substitution of a segment of the cellular genome with preselected isolated DNA, or by deletion of or inactivation of at least a portion of the cellular genome of the cell. Deletion or inactivation of at least a portion of the cellular genome can be accomplished by a variety of means including, but not limited to, genetic recombination, by antisense technology (which can include the use of peptide nucleic acids or PNAs), or by ribozyme technology, for example. Insertion of one or more preselected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The preselected gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA, as described by Sebestyen, et al. (*Nature Biotech.*, 16:80-85 (1998)), to direct the DNA to the nucleus for more efficient expression.

The genetic material can be introduced using promoters that will allow for the gene of interest to be positively or negatively induced using certain chemicals/drugs, to be eliminated following administration of a given chemical/drug, or can be tagged to allow induction by chemicals (including, but not limited to, the tamoxifen responsive mutated estrogen receptor) in specific cell compartments (including, but not limited to, the cell membrane).

Any of these techniques can also be applied to introduce a transcriptional regulatory sequence into stem cells or progeny to activate a desired endogenous gene. This can be done by either homologous (e.g., U.S. Pat. No. 5,641,670) or non-homologous (e.g., U.S. Pat. No. 6,602,686) recombination. These patents are incorporated by reference for teaching of methods of endogenous gene activation.

Successful transfection or transduction of target cells can be demonstrated using genetic markers in a technique that is known to those of skill in the art. The green fluorescent protein of *Aequorea victoria*, for example, has been shown to be an effective marker for identifying and tracking genetically modified hematopoietic cells (Persons et al., *Nature Medicine*, 4:1201-1205 (1998)). Alternative selectable markers include the β-Gal gene, the truncated nerve growth factor receptor, drug selectable markers (including, but not limited to, NEO, MTX, or hygromycin).

When the genetic modification is for the production of a biologically active substance, the substance will generally be one that is useful for the treatment of a given injury and/or disease. For example, it may be desired to genetically modify cells so they secrete a certain growth factor, growth factor receptor, cytokine, or extracellular matrix protein such as biglycan and/or fibromodulin.

The following examples are provided in order to demonstrate and further illustrate certain embodiments and aspects of the present invention and are not to be construed as limiting the scope thereof.

Example 1

Materials and Methods

This Example describes some of the materials and procedures used in the development of invention.

Animals

Experiments were performed using WT C57BL16, C57BL/6-TgN(ACTbEGFP)IOsb mice (Jackson Lab), or BGN$^{-/0}$/FMOD$^{-/-}$ and their strain matched WT mice (C57BU6-129) under an institutionally approved protocol for the use of animals in research. Generation of BGN$^{-/0}$/FMOD$^{-/-}$ deficient mice has been reported by Ameye et al., *FASEB J.*, 16:673-80 (2002).

Tendon Stem/Progenitor Isolation and Cultivation

Human tendon samples were obtained from patients undergoing tenotomy at Johns Hopkins University following approved guidelines set by National Institutes of Health Office of Human Subjects Research (OHSR 3005).

The human and mouse tendon specimens were first stripped of the tendon sheath and the surrounding paritendon when harvested allowing us to minimize the contribution of vascular cells in the preparations. The cells used in this study were, therefore, not from the surface of the tendon and were not tendon synovial cells, which are located at the tendon surface. The human tendon characterized was from the hamstring complex and consisted of 1 cm sample taken from the semitendinous tenotomy from children age 8-12. 3-4% of the tendon derived cells formed colonies and 95.9% of the P1 population was Stro-1 positive.

For mouse, patellar tendon was used. Murine patellar tendons were dissected from 6-8 week-old mice and digested with 3 mg/ml collagenase type I (Worthington) and 4 mg/ml dispase (Roche) in PBS for 1 hour at 37° C. Single cell suspensions were cultured (5% $CO_2$, 37° C.) in α-MEM (Gibco), supplemented with 20% fetal bovine serum (FBS, Equitech-bio), 2 mM glutamine, 100 U/ml penicillin/100 mg/ml streptomycin (Biofluids), and 100 mM 2-mercaptoethanol (Gibco) for 8-10 days.

Bone marrow stromal cells (BMSCs) were also isolated from the same patient or from the same mouse as described by Kunetsov et al., Br. J. Haematol., 97:561-70 (1997).

To isolate the TSPCs, density independent cell growth was employed, which is typically used to grow stem cells and transiently amplified cells. In order to isolate pure stem/progenitor cell population, low density single cell suspensions were used to exclude mature cell populations. When the tendon derived single cell suspensions were plated they were quiescent for ~5-6 days after which they proliferated rapidly Single cell suspensions of tendon-derived cells were cultured for colony forming efficiency assays in a 25 cm$^2$ flask for 9 days, and then stained with an aqueous solution of saturated methyl violet (Sigma) after fixation with 100% methanol. Cell clusters with more than 50 cells were scored as colonies. The proliferation of tendon stem/progenitor cells (TSPCs) and BMSCs (first passage) was assessed by BrdU incorporation for 24 hours (Zymed), where the BrdU positive cells were detected using the BrdU Staining Kit (Zymed) following procedures recommended by the manufacturer.

Murine Dermal Fibroblast Cell Isolation and Culture

Shaved skin were dissected from 6-8 week-old mice, cut into 1 cm$^2$ pieces and placed dermis-side down in a 100 mm petri dish. The skin samples were digested with 0.25% trypsin (Gibco) and 4 mg/ml dispase (Roche) in PBS overnight at 4° C. and 2 hours at 37° C. The epidermis was peeled from the digested skin samples. The dermis was cut into fine pieces and digested with 400 units/ml collagenase type II (Worthington) for 1 hour. The digested tissue solution was passed through a 70 μm cell strainer. Cell suspensions were cultured (5% $CO_2$, 37° C.) in DMEM (Gibco), supplemented with 10% fetal bovine serum (FBS, Equitech-bio) and 100 U/ml penicillin/100 mg/ml streptomycin (Biofluids) for 2-3 days. The TSPCs were analyzed at either P1 for mouse and at P1 or P2 for human.

Multipotent Differentiation

The in vitro multi-differentiation potential of the TSPCs was tested toward osteogenesis, adipogenesis, and chondrogenesis as described by Bi et al., J. Biol. Chem., 280:30481-30489 (2005); Gimble et al., J. Cell Biochem., 58:393-402 (1995); Johnstone et al., Exp. Cell Res., 238:265-72 (1998). Osteogenic differentiation of TSPCs was quantified by measuring the intensity of Alizarin Red S staining $Ca^{2+}$ (Kostenuik et al., Am. J. Physiol., 273:E1133-39 (1997)) and normalized to cell number. The number of the cells in each well was determined with Cell Count Kit-8 (Dojindo). The adipocytes were visualized by staining with 0.3% Oil Red O (Sigma). The stain was solublized with isopropanol for 30 minutes at room temperature and measured at 490 nm. The adipogenic differentiation was determined by the amount of Oil Red O in each well that was normalized to cell number. The chondrogenic differentiation of TSPCs was assessed by staining paraffin embedded sections with toluidine blue, safranin O, or for type II collagen. The multi-differentiation potential of the TSPCs was also examined using an in vivo transplantation system as described by Bi et al., J. Biol. Chem., 280:30481-30489 (2005) and Krebsbach et al., Transplantation 63:1059-69 (1997). TSPCs were first cultured in vitro in osteogenic induction medium for 2 weeks in the presence of 100 ng/ml BMP2 (Wyeth) before being mixed with hydroxyapatite-tricalcium phosphate (HA-TCP) (Zimmer International Inc., Warsaw, Ind.) and then transplanted subcutaneously into the dorsal surface of immunocompromised beige mice (NM-bg-nu-xid, Harlan Sprague Dawley, Indianapolis, Ind.) for 8-9 weeks. Multipotent differentiation of TSPCs was assessed by staining paraffin embedded sections with hematoxylin and eosin (H&E), Alcian blue, Trichrome (Masson's or Goldner's), or for type I collagen.

Label-Retaining Cells

BrdU (Sigma, 50 mg/g body weight) was injected intraperitoneally into 3 day-old pups twice a day for 3 days. At the indicated times, mouse knees were fixed (4% paraformaldehyde in PBS, 3 days), decalcified (10% EDTA, pH 8.0, 7-10 d) at room temperature, and paraffin-embedded mouse knees. BrdU labeled cells were detected on the paraffin embedded sections using the BrdU Staining Kit (Zymed) following procedures recommended by the manufacturer.

Western Blotting

Confluent TSPCs or BMSCs were treated with 100 ng/ml BMP2 or vehicle for the indicated times. The protein extraction and Western blot analyses were performed as described in Bi et al., J. Biol. Chem., 280:30481-30489 (2005). The primary antibodies included: rabbit anti-p-Smad1, rabbit anti-Smad1 (1:500, Cell Signaling), rabbit anti-Hsp 90 (1:500, Santa Cruz) and rabbit anti-Cbfa1 (1:100, Oncogene).

FACS Analysis

Cells ($5 \times 10^5$) were incubated with 1 μg of PE- or FITC-conjugated rat anti-mouse or mouse anti-human monoclonal antibodies for 1 hour at 40° C. PE- or FITC-conjugated isotype-matched IgGs (Pharmingen) were used as controls. After three washes with PBS containing 1% FBS and 0.01% azide, the stained cells were subject to FACS analysis (Becton Dickinson). The percentage of the cell population in each quadrant was calculated using the FACSCAN program.

All antibody conjugates were purchased from Pharmingen/BD Biosciences unless specifically mentioned, which included PE-conjugated rat anti-mouse CD18 (C71/16, IgG2a, kappa), CD117 (c-kit, 2B8, IgG2b, kappa), CD45 (30-F11, IgG2b, kappa) and Flk-1 (Avas 12a1, IgG2a, kappa), FITC-conjugated rat anti-mouse Sca-1 (E13-161.7, IgG2a, kappa), CD34 (49E81, IgG2a, kappa), CD44 (IM7, IgG2b, kappa) CD90.2 (53.2.1, IgG2a, kappa, Stemcell Technologies Inc. Vancouver, Canada), PE-conjugated mouse anti-human CD18 (clone 6.7, IgG1, kappa), CD44 (515, IgG1, kappa), CD117 (c-kit, YB5.B8, IgG1, kappa), CD90 (5E10, IgG1, kappa), and FITC-conjugated mouse anti-human CD45 (H130, IgG1, kappa), CD34 (581, IgG1, kappa), CD106 (51-10C9, IgG1, kappa), CD146 (MUC18, P11-112, IgG1, kappa).

For non-conjugated rat anti-mouse CD144 (11D4.1, IgG2a, kappa) or mouse anti-human Stro-1 (IgM) Abs, they were incubated with $1 \times 10^{-6}$ cells for 1 hour at 4° C. After washing, the cells were incubated with secondary detection reagents, either goat anti-rat IgG2a- or goat anti-mouse IgM-FITC conjugated Abs (Southern Biotechnology Associates) for 45 minutes on ice. After washing, the samples were analyzed using an Epics-XL-MCL flow cytometer (Beckman Coulter).

RT-PCR

Total RNA was isolated from confluent TSCs or BMSCs using Trizol (InVitrogen) and cDNA obtained by reverse transcribing total RNA with 50 units of Superscript II RT using random hexamer primers (InVitrogen). The primers were designed with Primer 3 software (genome.wi.mit.edu/cgibin/primer/primer3.cgi) and are listed as follows.

For the mouse samples:

```
scleraxis:
forward
5'aacacggccttcactgc3'                    (SEQ ID NO: 8)

reverse
5'cttcgaatcgccgtctt3'                    (SEQ ID NO: 9)

COMP:
forward
5'cgcagctgcaagacgtgagagagctgt3'          (SEQ ID NO: 10)

reverse
5'ccgaattccgctggtctgggtttcga3'           (SEQ ID NO: 11)

sox 9:
forward
5'tcagatgcagtgaggagcac3'                 (SEQ ID NO: 12)

reverse
5'ccagccacagcagtgagtaa3'                 (SEQ ID NO: 13)

Runx2:
forward
5'gcagttcccaagcatttcat3'                 (SEQ ID NO: 14)

reverse
5'cactctggctttgggaagag3'                 (SEQ ID NO: 15)

osterix (sp7):
forward
5'aagtgtgtgtgccgtggata3'                 (SEQ ID NO: 16)

reverse
5'gtcgagaggactggggtaca3'                 (SEQ ID NO: 17)

osteopontin (opn):
forward
5' cgatgatgatgacgatggag3'                (SEQ ID NO: 18)

reverse
5' gaggtcctcatctgtggcat3'                (SEQ ID NO: 19)

bone siaoloprotein (BSP):
forward
5' attttgctcagcattttggg3'                (SEQ ID NO: 20)

reverse
5' ctgaagagtcactgcctccc3'                (SEQ ID NO: 21)

alkaline phosphatase (AP):
forward
5' ccagcaggtttctctcttgg3'                (SEQ ID NO: 22)

reverse
5' ctgggagtctcatcctgagc3'                (SEQ ID NO: 23)

aP2:
forward
5' gaagcttgtctccagtcaaaa3'               (SEQ ID NO: 24)

reverse
5'agtcacgcctttcataacacat3'               (SEQ ID NO: 25)

C/EBPG:
forward
5' ttacaacaggccaggtacc3'                 (SEQ ID NO: 26)

reverse
5' ctctgggatggatcgattgt3'                (SEQ ID NO: 27)

LPL:
forward
5' gtctggctgacactggacaa3'                (SEQ ID NO: 28)

reverse
5' tgggccattagattcctcac3'                (SEQ ID NO: 29)

gapdh:
forward
5'gagaggccctatcccaactc3'                 (SEQ ID NO: 30)

reverse
5'gtgggtgcagcgaactttat3'                 (SEQ ID NO: 31)

β-actin:
forward
5' agccatgtacgtagccatcc3'                (SEQ ID NO: 32)

reverse
5' ctctcagctgtggtggtgaa3'.               (SEQ ID NO: 33)
```

For human samples:

```
COMP:
forward
5'agaacatcatctgggccaac3'                 (SEQ ID NO: 34)

reverse
5'tcctctctgagcccttctca3'                 (SEQ ID NO: 35)

tenomodulin:
forward
5'ccatgctggatgagagaggt3'                 (SEQ ID NO: 36)

reverse
5'ccaccagttacaaggcatga3'                 (SEQ ID NO: 37)

runx2:
forward
5'cagttcccaagcatttcatcc3'                (SEQ ID NO: 38)

reverse
5'tcaatatggtcgccaaacag3'                 (SEQ ID NO: 39)

osterix:
forward
5'gccagaagctgtgaaacctc                   (SEQ ID NO: 40)

reverse
5'gctgcaagctctccataacc                   (SEQ ID NO: 41)

alkaline phosphatase (AP):
forward
5'aagaaaggggacccaagaaa3'                 (SEQ ID NO: 42)

reverse
5' gtactctctgcctgcccaag3'                (SEQ ID NO: 43)

osteocalcin (ocn):
forward
5' tggcaggctctacacagaga3'                (SEQ ID NO: 44)

reverse
5' tttcagccgttctcagaggt3'                (SEQ ID NO: 45)

LPL:
forward
5' atggagagcaaagccctgctc3'               (SEQ ID NO: 46)

reverse
5' gttaggtccagctggatcgag3'               (SEQ ID NO: 47)

C/EBPα:
forward
5' tggacaagaacagcaacgag3'                (SEQ ID NO: 48)

reverse
5' ttgtcactggtcagctccag3'                (SEQ ID NO: 49)
```

```
-continued adipson:
forward
5' gcgcacctggcgcaggcgtcctg3'    (SEQ ID NO: 50)

reverse
5' gcactgcgcgcagcacgtcgta3'     (SEQ ID NO: 51)

PPARγ:
forward
5' ccggagaacaatcagattgaagc3'    (SEQ ID NO: 52)

reverse
5' cgcctttgctttggtcagcgg3'      (SEQ ID NO: 53)

gapdh:
forward
5' cgaccactttgtcaagctca3'       (SEQ ID NO: 54)

reverse
5'aggggtctacatggcaactg3.        (SEQ ID NO: 55)
```

PCR was performed using GOTAG® (Promega, Madison, Wis.) or with incubation at 94° C. for 5 minutes followed by 35 cycles of a three temperature program of 1 minute at 94° C., 20 seconds at 57° C., and 30 seconds at 72° C. The PCR reaction was terminated after a 7 min extension at 70° C. and the entire reaction was chilled and stored at 4° C. until analysis. Five microliters of the PCR product and a 0.25 microgram of X174RFDNA/HaeIII DNA ladder (Gibco) were run in a 6% acrylamide gels in (TBE) buffer at 100 V. The separated DNA fragments were visualized after syber safe staining under a UV light.

Nucleofection and Luciferase Reporter Assays

Activation of the BMP signaling pathway was determined using a BMP responsive luciferase reporter construct pID1-lux. Sharma et al., J. Musculoskel. Neuronal. Interact., 6:181-90 (2006). This construct contains a fragment of the human Id1 gene minimal promoter (−170 to +86) which contains multiple smads binding sites. Transient transfection of primary tendon cultures was carried out using the Nucleofector system (AMAXA, Germany) and the mesenchymal stem cells transfection kit modified for use with tendon stem cells. Optimal transfection conditions were first determined using a construct containing GFP to achieve approximately 60-80% transfection efficiency for approximately 72 hours. Briefly, tendon stem cells ($5\times10^5$ cells, passage 2) were placed in transfection solution with 2 µg total DNA, and subjected to electroporation using the program C-17. Transfections with the pID-lux construct as well as an internal control phSV40 renilla luciferase (20:1 ratio) were compared to parallel transfections with a control pGL3 vector. The transfected cells were plated into 3 wells of 96 well plates and cultured for 24 hours. After cells were treated with 100 ng/ml BMP2 overnight in culture medium containing 5% serum, luciferase activity was measured using the dual reporter assay system (Promega, Madison, Wis.). Luicferase activity was normalized to relative renilla activity within the same well.

In Vivo Transplantation

Tendon stem cells were transplanted subcutaneously onto calvariae or into the dorsal surface of 8-10 week-old immunocompromised beige mice as described in ACUC #NIDCR-DIR-05-347; and Kannus, Scand. J. Med. Sci. Sports, 10:312-20 (2000). Approximately $2-2.5\times10^6$ cells were mixed with 40 mg of HA/TCP ceramic powder (Zimmer), GELFOAM® (3 mm×3 mm×2 mm, Pharmacia, Piscataway, N.J.) or 20 ml MATRIGEL® (BD Biosciences, Bedford, Mass.). Transplants were harvested after 8-9 weeks, fixed (4% paraformadehyde in PBS, 25° C., 3 days), decalcified (10% EDTA, pH 8.0, at 25° C.), and then embedded in paraffin.

Immunocytochemistry

The primary antibodies used in this study included rabbit anti-GFP polyclonal antibody (IgG, 4 µg/ml, Santa Cruz), mouse anti-type II collagen (1:50, 4 µg/ml, Chemicon), mouse anti-α-smooth muscle actin (1:100, 0.7 µg/ml, DakoCytomation, Denmark), mouse anti-fibronectin (1:500, 0.4 µg/ml, Chemicon), rat anti-tenascin C (1:100, 5 µg/ml, R&D system), rabbit anti-aggrecan (1:100, 5 µg/ml, Chemicon), anti-phospho-Smad1/5/8 (1:100, 1.6 µg/ml, Cell Signaling), anti-type I collagen (rabbit total serum, 1:2000 dilution), anti-COMP (rabbit total serum, 1:1500 dilution). Isotype-matched negative control antibodies were used under the same conditions.

The transplant-derived TSPC colonies or TSPCs (passage 1) were fixed (4% paraformaldehyde in PBS, 25° C., 20 minutes) and immunostained with primary antibodies (described above) for 1 hour at room temperature or overnight at 4° C. The broad-spectrum immunoperoxidase AEC kit was subsequently used to detect the immunoactivity according to the manufacturer's instruction. The cells were counterstained with hematoxylin.

Histochemistry and Immunohistochemistry

Paraffin embedded sections were stained histochemically for hematoxylin and eosin (H&E), toluidine blue, safranin O, or trichrome (Masson's or Goldner's). For immunohistochemical analysis, sections were immunolabeled using primary antibodies at 25° C. for 1 hour, including anti-type I collagen, anti-BGN, anti-FMOD (rabbit total serum 1:500 dilution), anti-type II collagen (Mouse IgG, 1 Chemicon, Temecula, Calif.), rabbit anti-aggrecan (1:100, 5 Chemicon) and anti-GFP (rabbit IgG, 4 µg/ml, Santa Cruz). Isotype-matched negative control antibodies were used under the same conditions. The broad-spectrum immunoperoxidase AEC kit (Picture Plus, Zymed) was subsequently used to detect the immunoactivity according to the manufacturer's instructions. The sections were counter stained with hematoxylin.

Microcomputed Tomography Analysis (µCT)

Mouse knees were scanned and reconstructed with 15 mm isotropic voxels on a µCT system (eXplore MS, GE Medical Systems, London, Ontario, Canada). The 2-D and 3-D imagines of the knee region were revealed using Microviewer (GE Medical Systems).

Statistical Analysis

Representative figures of at least three independent experiments are reported herein. Statistical analyses was performed with student's t-test and presented data as mean±SEM (n=3 or more).

Example 2

Tendon Stem Cell Isolation and Characterization

This Example describes the isolation of a rare cell population from both human and mouse tendons and shows that they possess several universal criteria of stem cells including 1) clonogenic, 2) self-renewal and 3) multipotent differentiation capacity. These tendon stem cell reside within a niche composed primarily of the extracellular matrix of tendons, which is unique among the known stem cell niches, including the bulge niche for skin stem cells, the osteoblast niche for hematopoietic stem cells, and the perivascular niche for neural stem cells and bone marrow mesenchymal stem cells (MSCs). In addition, genetically engineered mice were used to identify BGN and FMOD as the two critical components of the tendon stem cell niche, which control the fate of tendon stem cell in part by modulating BMP activity.

The materials and methods used for obtaining the following results are described in Example 1.

Figure 1B:
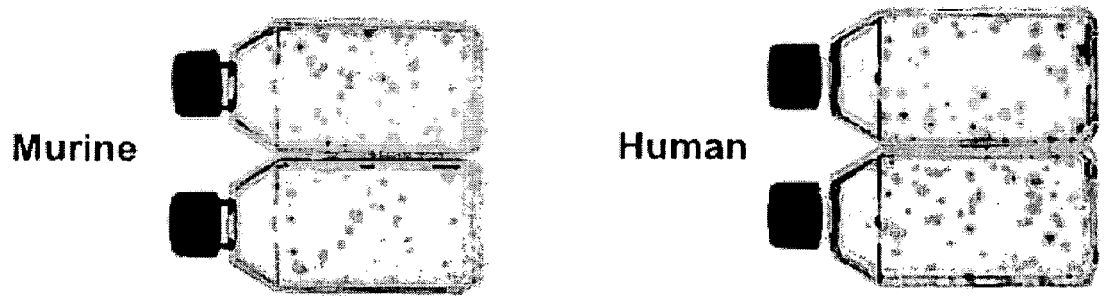

Tendon-derived cells possess clonogenic capability. The commonly used criteria that define stem cells are their clonogenic, self-renewal and multipotent capabilities. To characterize whether tendon-derived cells are clonogenic, single cell suspensions were generated by digesting tendons with dispase and type I collagenase, and cultured for 8-10 days. A portion of tendon-derived cells attached to the plate and remained quiescent for 5-6 days before they started rapidly dividing to form colonies. At days 8-10, colonies formed from single cell were visualized after methyl violet staining (FIGS. 1A-B). A small population (about 3-4%) of tendon-derived cells from both mouse and human tissue formed adherent cell colonies (FIG. 1B), which were termed Tendon Stem/Progenitor Cells (TSPCs) (FIG. 1A). These colonies were heterogeneous in size and cell density, indicating a potential difference in the rate of cell proliferation (FIG. 1A). Morphologically, five different colony types were observed in murine tendon-derived cell cultures (TSPCs-1-5, FIG. 1C) and their morphology was different from that of bone marrow stromal cells (BMSCs, FIG. 1C). Human tendon-derived cells (hTSPCs) were relatively homogeneous and similar to human BMSCs (hBMSCs, FIG. 1C).

Figure 1C:
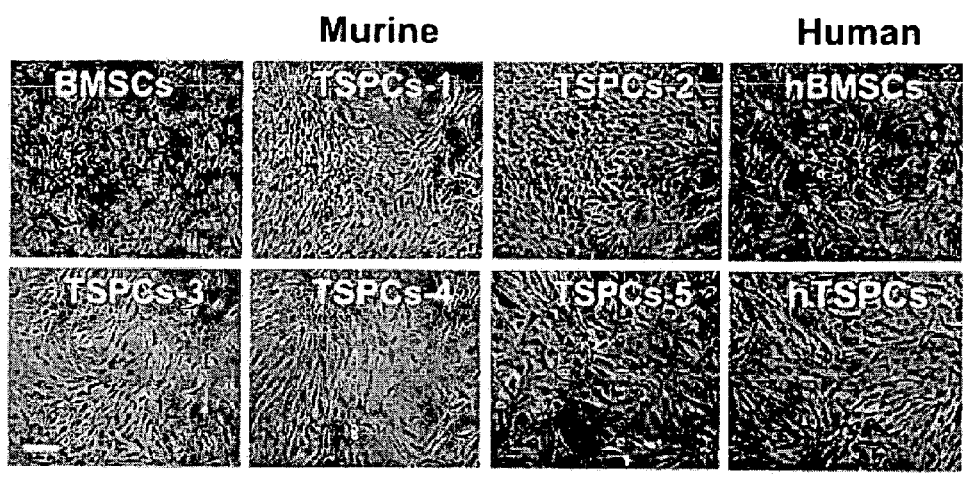
Figure 1D:
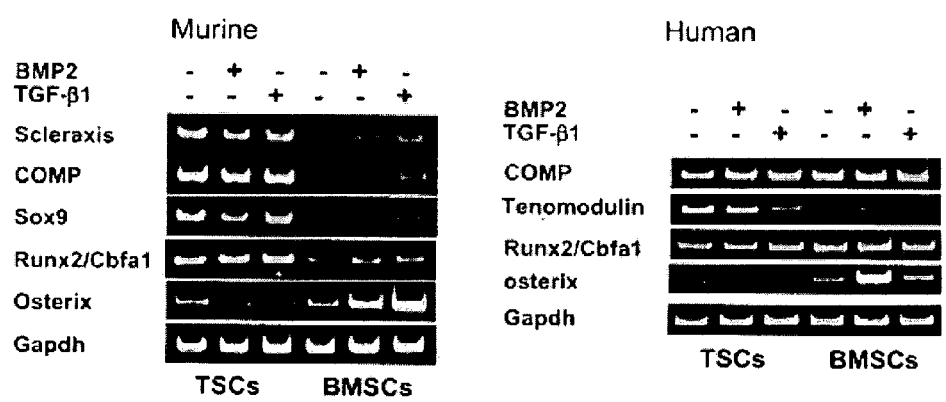

Tendon-derived cells express genes distinct from bone marrow stromal cells. Mouse and human TSPCs and BMSCs were isolated from post-natal tendon tissues and bone marrow, respectively, and were then expanded in vitro prior to mRNA isolation and assessment. Semi-quantitative RT-PCR showed that murine TSPCs expressed higher levels of scleraxis (a twist-related bHLH transcription factor) (Brent et al., Cell, 113:235-48 (2003)), cartilage oligomeric protein (COMP) (DiCesare et al., Eur. J. Biochem., 223:927-937 (1994)), sox9 (Akiyama et al., Genes Dev., 16:2813-2828 (2002)), and osteogenic transcription factor, Runx2/cbfa1 (Komori et al., Cell, 89:755-764 (1997)), whereas BMSCs expressed more abundantly its downstream effector, osterix (Nakashima et al., Cell, 108:17-29 (2002)) (FIG. 1D). In addition, BMP2 and TGF-β inhibited TSPC expression but promoted BMSC expression of those factors. Human TSPCs expressed higher levels of tenomodulin (Brandau et al., Dev. Dyn., 221:72-80 (2001)) compared to BMSCs (FIG. 1D), whereas human BMSCs expressed high levels of osterix (FIG. 1D). BMP2 and TGF-β1 are important growth factors in the regulation of tendon and bone formation. Therefore, we examined how TSPCs and BMSCs response to these factors. BMP2 and TGF-β1 inhibited TSPC expression of scleraxis, Sox9 and tenomodulin but promoted BMSC expression of Runx2/cbfa1 and Osterix. Osterix was highly induced by BMP2 in BMSCs. The expression levels of COMP were similar in both human TSPCs and BMSCs (FIG. 1D) and were not affected by BMP2 and TGF-β3 treatment.

Figure 1E:
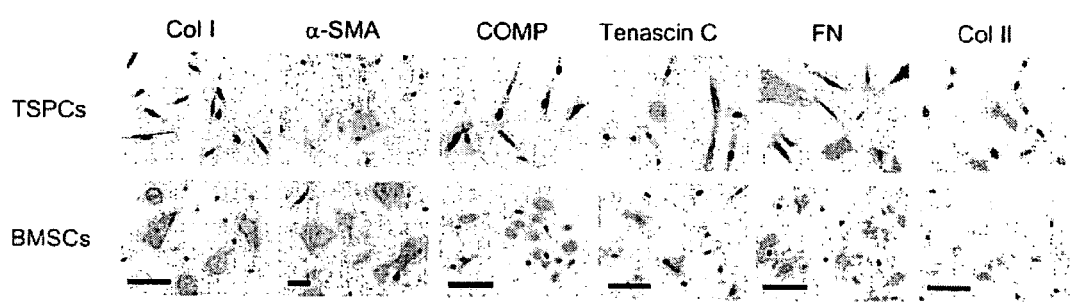

Immunocytochemistry staining further confirmed the unique phenotype of the isolated TSPCs. Specifically, all TSPCs expressed type I collagen whereas only a certain population of BMSCs expressed this protein (FIG. 1E). On the other hand, expression of α-SMA was more abundant in BMSCs than in TSPCs (FIG. 1E). Consistent with the RT-PCR results (FIG. 1D), relatively more TSPCs than BMSCs expressed COMP and tenascin C. All TSPCs and BMSCs expressed fibronectin, but none expressed type II collagen (FIG. 1E).

Figure 1F:
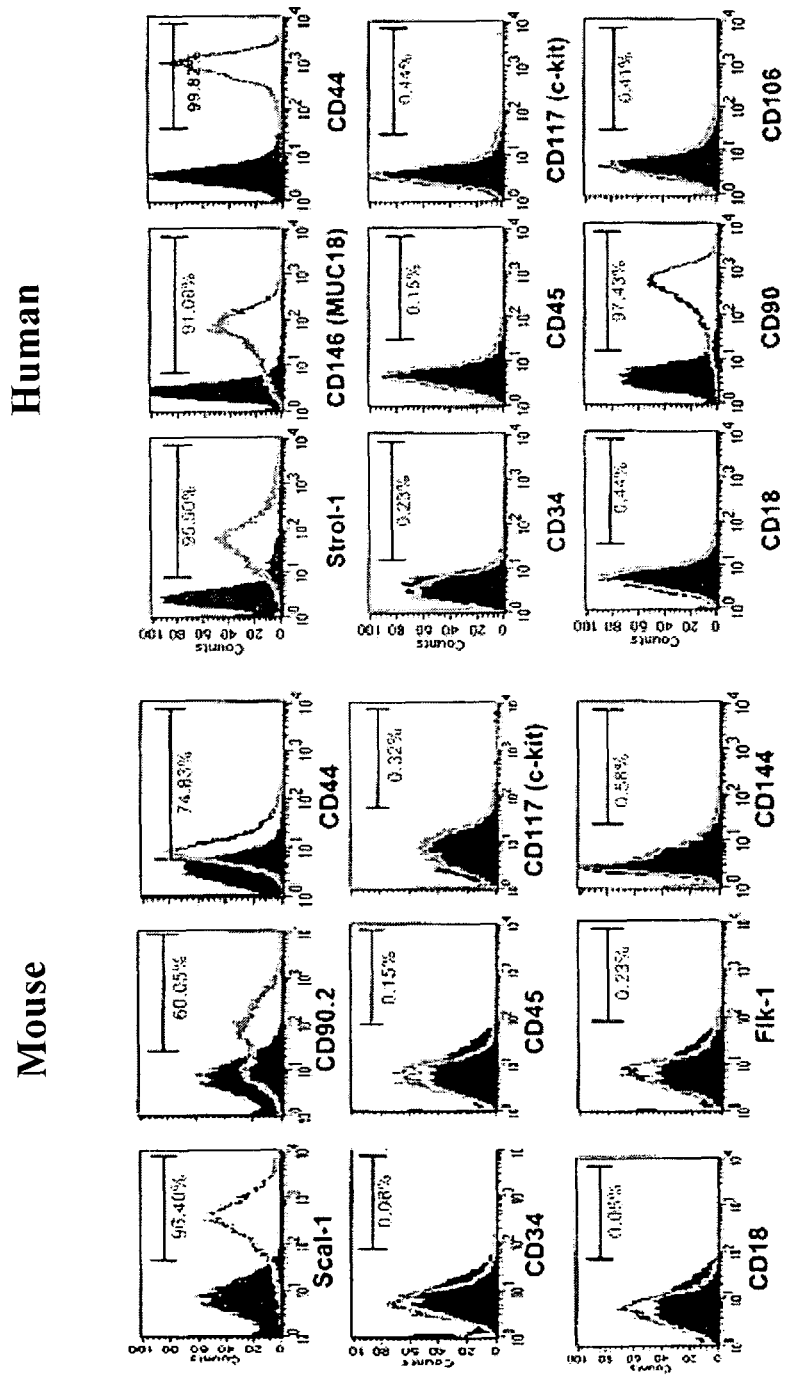
Figure 1G:
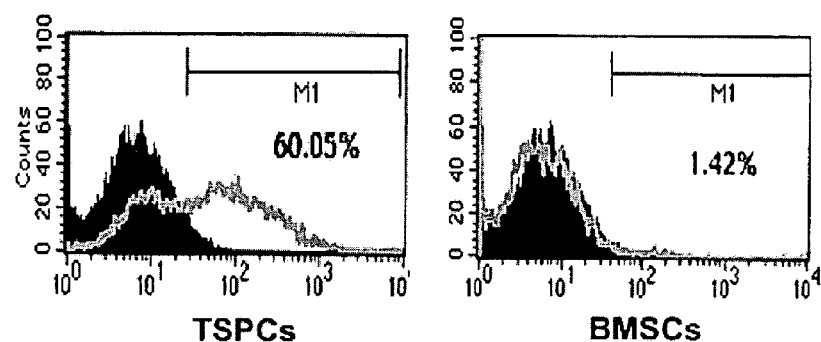

Flow cytometric analysis was used to examine the presence of surface antigens on TSPCs (FIG. 1F). Over 96% of murine TSPCs (passage 0) were positive for a stem cell marker, stem cell antigen-1(Sca-1) (Spangrude et al., Science, 241:58-62 (1988); VanVlasselaer et al., Blood, 84:753-763 (1994); Gussoni et al., Nature, 401:390-394 (1999); Tamaki et al., J. Cell Biol., 157:571-577 (2002); Welm et al., Dev. Biol., 245:42-56 (2002)). Moreover, over 60% of these cells were positive for the fibroblast marker CD 90.2 that was not expressed by BMSCs (FIGS. 1F-G). In addition, the TSPCs were negative for CD34 and CD117 (hematopoietic stem cell markers), CD45 (a leukocyte marker), and Hk-1 and CD144 (endothelial cell markers), thus verifying the lack of contaminating hematopoietic cells and endothelial cells (FIG. 1F). TSPCs were positive for CD44, but not CD18, a surface receptor present on BMSCs 25 (FIG. 1F). Similarly, human TSPCs (passage 2) were positive for BMSCs markers, Stro-1, CD146 (Muc18) 26327, CD 90, and CD44, but not for CD18, (FIG. 1F). Like murine TSPCs, human TSPCs did not express hematopoietic cell markers, CD34, CD45 and c-kit or the endothelial cell marker, CD106 (FIG. 1F). The putative tendon stem cells have multipotent differentiation potential.

Figure 2A:
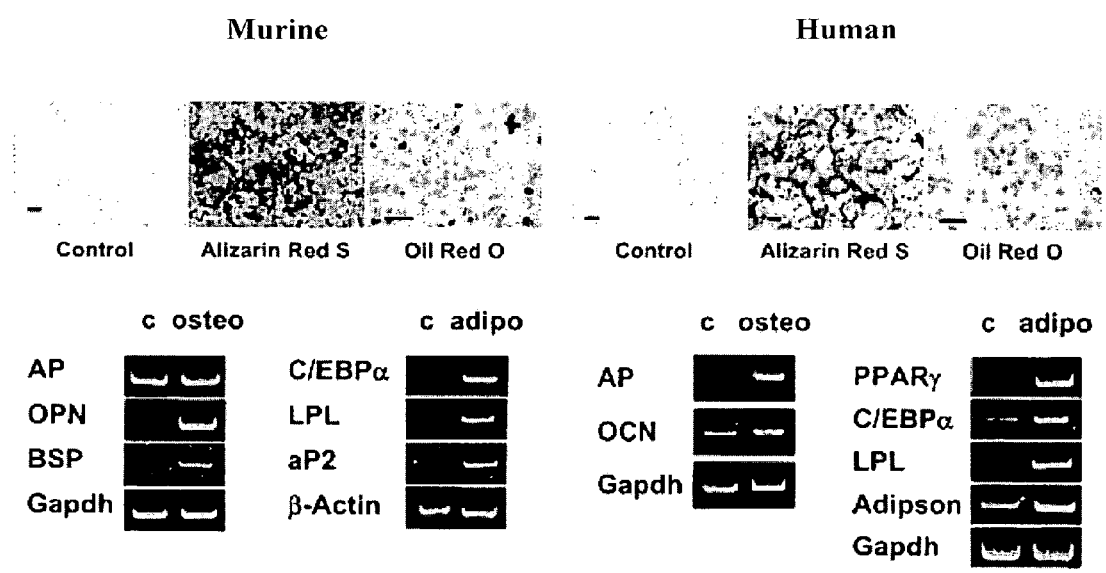
FIGS. 2A-2G illustrate the multi-differentiation potential of putative murine and human tendon stem cells in vitro and in vivo.
Figure 2B:
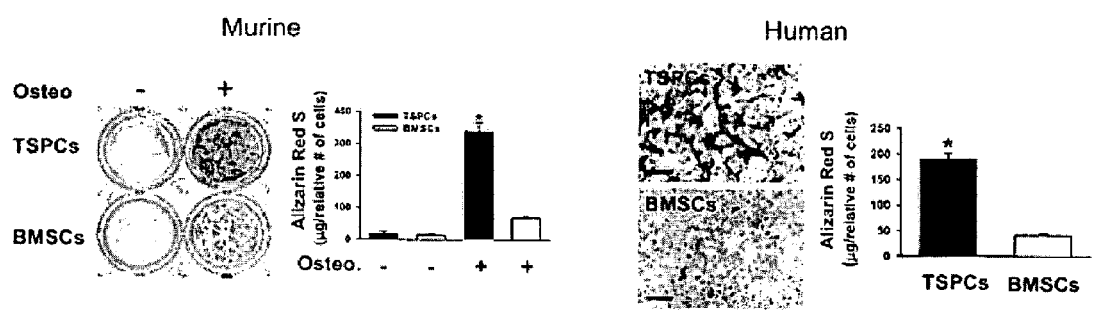
Figure 2C:
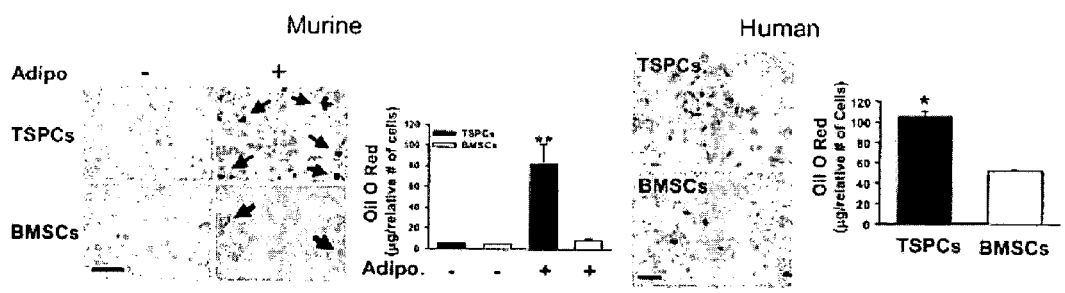
Figure 2D:
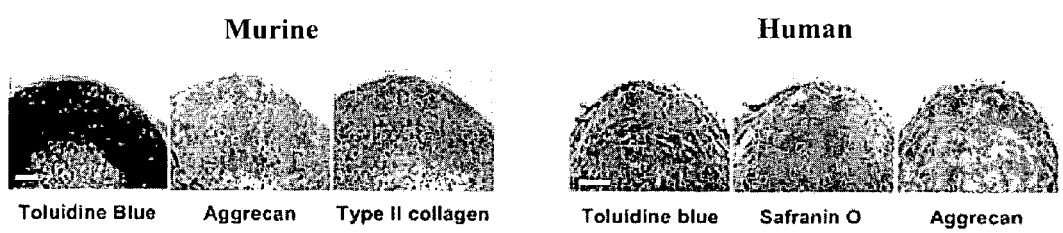

The multi-differentiation potential of the TSPCs toward osteogenesis, adipogenesis and chondrogenesis was determined and then compared to the multi-differentiation properties of BMSCs. Murine and human TSPCs accumulated $Ca^{2+}$ more rapidly (about 4 times) and formed more nodules than BMSCs (FIGS. 2A-B). RT-PCR analysis showed that expression of osteogenic markers, osteopontin (OPN), bone sialoprotein (BSP), alkaline phosphatase (ALP) and osteocalcin (OCN) was increased after osteogenic induction for 3 weeks. Oil Red O staining of the lipid droplets within the adipocytes, which is an indicator of adipogenesis, was also greater in TSPCs after 3 weeks of culture in adipogenic induction medium (FIGS. 2A and 2C). The expression of LPL, C/EBPa, aP2, adipson and PPARy mRNAs were also induced after 3 weeks of adipogenic induction. Chondrogenic differentiation was assessed after induction in chondrogenic medium in pellet culture by type II collagen and aggrecan expression and by toluidine blue and safranin O staining of the proteoglycan-rich extracellular matrix (FIG. 2D). As the passage number increased, the TSPCs did have somewhat altered mutipotential differentiation capacity has been observed for BMSC. However the ability to form tendon-like tissue did not change after many passages.

Figure 2E:
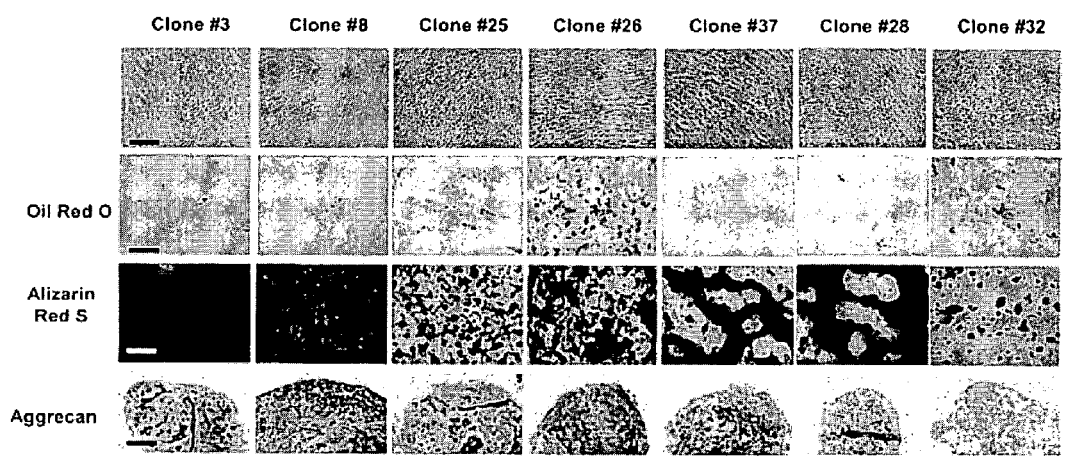
Figure 2F:
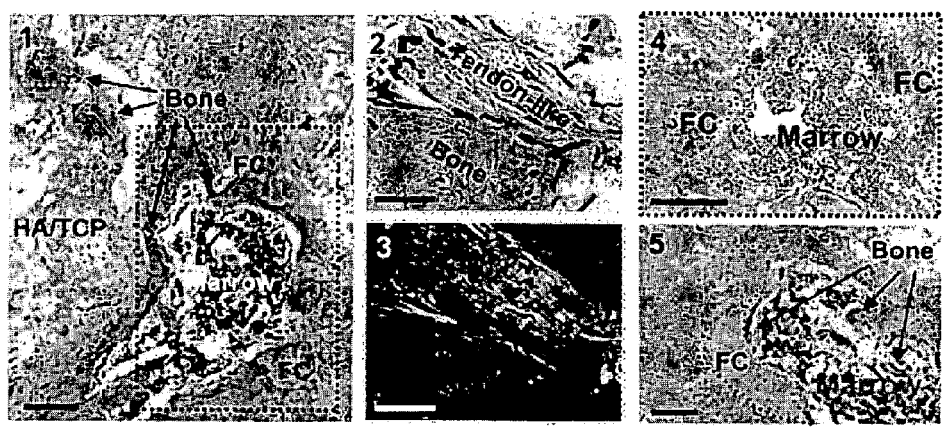
Figure 2G:
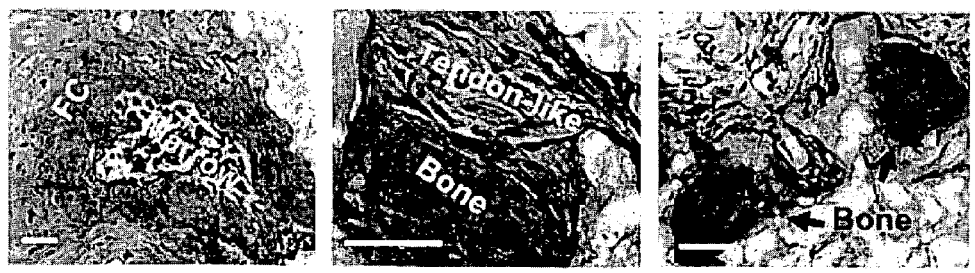

Like human BMSCs, individual colonies of human TSPCs showed heterogeneous differentiation potential toward osteogenesis, adipogenesis and chondrogenesis (FIG. 2E). The majority of colonies (14 out of 18 colonies from 2 donors) showed three-way potential. A small percentage of colonies showed only two-way potential (3 out of 18 colonies) and/or one potential (1 out of 18 colonies). To determine the multi-differentiation potential of TSPCs in vivo, these cells were cultured in osteogenic induction medium in the presence of BMP2 for 2 week before being transplanted subcutaneously with a carrier (hydroxyapatite/tricalcium phosphate, HA/TCP) into immunocompromised mice. Bi et al., J. Biol. Chem., 280:30481-30489 (2005); Krebsbach et al., Transplantation, 63:1059-1069 (1997). Bone formation was observed on the WTCP carrier surface (FIG. 2F1), and tendon-like tissues were observed adjacent to the newly formed bones (FIG. 2F2), which was further confirmed by the presence of unique collagen fibers under polarized light (FIG. 2F3) and by Goldner's trichrome staining (FIG. 2G). Bone marrow-like structures were found at the center of the newly formed bones and were surrounded by fibrocartilages (FC, FIG. 2F1), as evidenced by positive alcian blue (FIG. 2F4) and negative type I collagen staining (FIG. 2F5).

When the TSPCs were treated with BMP-2 (to induce them to differentiate into bone cells) they formed sheets and generally needed to be treated at least 10-15 minutes in the presence of trypsin to generate single cells and small clumps of cells. The small clumps of cells did not hinder the ability of TSPCs to form bone in vivo when they were transplanted in combination with HA/TCP. In order to obtain single cell suspension without any clumps, treatment with collagenase was needed to dissociate the cells from the matrix.

Figure 3A:
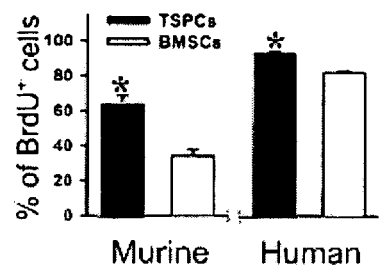
FIGS. 3A-3H illustrate the self-renewal of tendon stem cells.
Figure 3B:
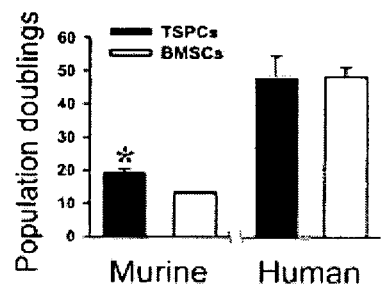
Figure 3C:
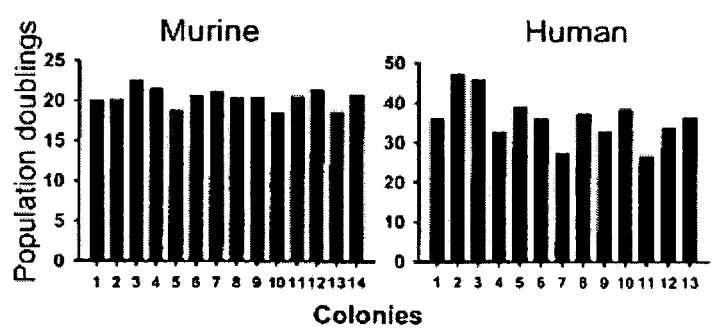
Figure 4:
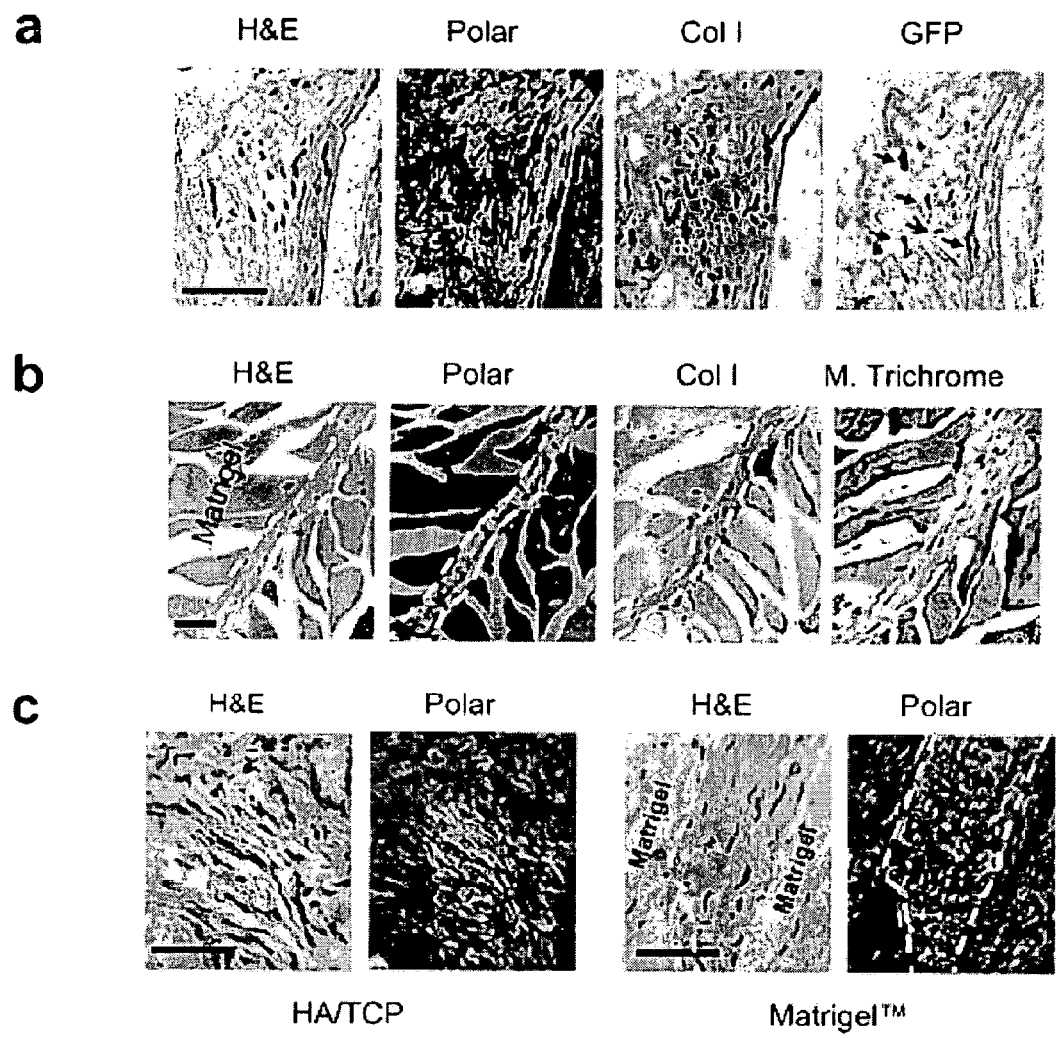
FIGS. 4A-4F illustrate the regeneration potential of putative tendon stem cells. Murine TSPCs formed tendon-like tissue in vivo 8 weeks after transplantation with HA/TCP ceramic powder (FIG. 4A) or MATRIGEL® (FIG. 4B). Tendon-like tissues were identified using polarized light (polar), Masson's trichrome and type I collagen staining (Col I, brown color). The origin of the tendon-like tissues was identified by GFP staining (black arrow). Bars=50 µm.

The putative tendon stem cells have self-renewal capability. Both human and mouse TSPCs proliferated faster than BMSCs isolated from the same patient or animal (FIG. 3A), as judged by BrdU incorporation. Population doubling assays showed that both murine and human TSPCs could divide for an extensive period of time in vitro (FIG. 3B). The population doubling of murine TSPCs was higher than that of BMSCs, but this was not observed for human TSPCs (FIG. 3B). Furthermore, TSPCs derived from individual colonies exhibited a high proliferation capability for an extended period of time (FIG. 3C).

Figure 3D:
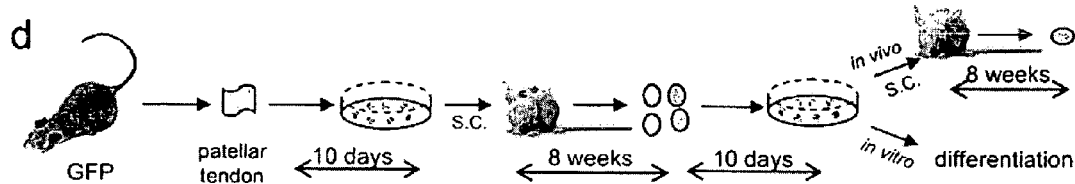
Figure 3E:
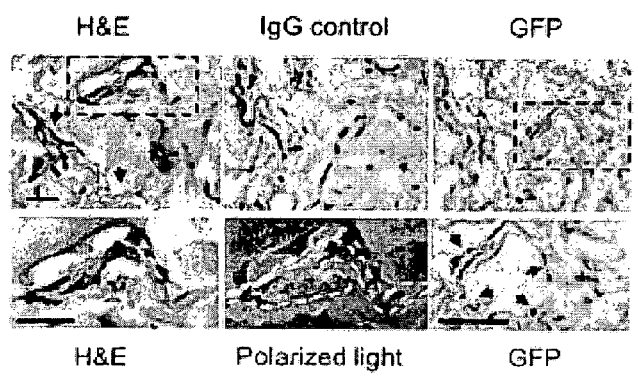
Figure 3F:
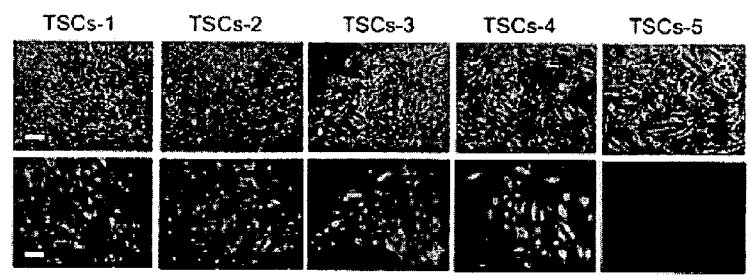
Figure 3G:
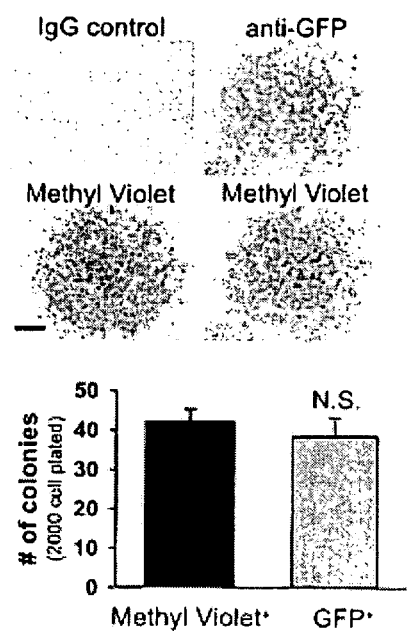
Figure 3H:
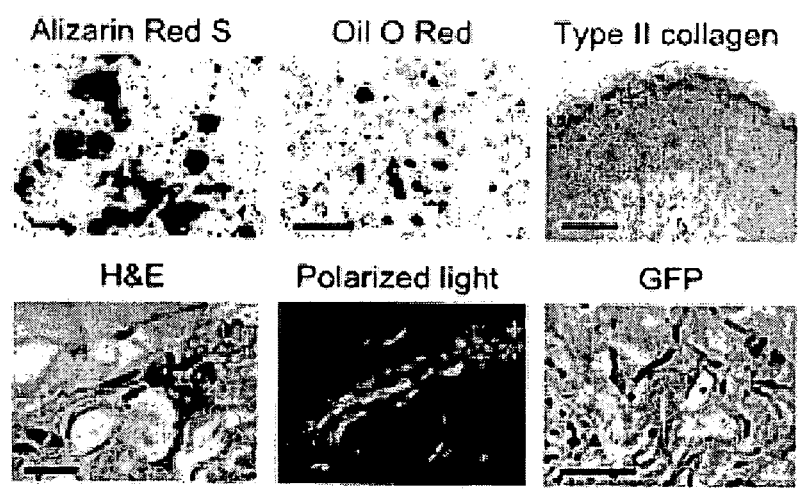

The high doubling capacity of TSPCs suggested that they possess self-renewing capability. To confirm this, TSPCs were examined for their clonogenic and multi-differentiation potential after serial in vitro and in vivo expansions (FIG. 3D). Briefly, TSPCs were isolated from GFP transgenic mice, expanded in vitro, and then transplanted subcutaneously with GELFOAM® into the dorsal surface of immunocompromised mice. After 8 weeks, tendon-like tissues formed in the transplants that contained GFP positive cells, indicating their donor cell origin (FIG. 3E). The transplants were removed, digested with collagenase/dispase, and then expanded again in vitro. The transplant-derived GFP-positive TSPCs retained their ability to form colonies (FIG. 3F) with a slightly lower colony-forming efficiency (about −2%; FIG. 3G). Approximately 90% of the colonies were GFP positive, as determined by fluorescent microscopy (FIG. 3F) and by anti-GFP antibody staining (FIG. 3G). A few GFP-negative cell clusters were observed in the culture, resulting from contamination of the host tissue (FIG. 3F, TSPCs-5). Morphologically, they exhibited clonal heterogeneity similar to those of primary tendon-derived TSPC cultures (FIGS. 3F and 1C). Most importantly, the transplant-derived TSPCs retained their ability to differentiate into osteoblasts, adipocytes and chondrocytes (FIG. 3H), as well as their ability to form tendon-like tissues in vivo, when re-transplanted with Gelfoam™ (FIG. 3H). These data demonstrated that even after extended expansion in vitro and in vivo, the TSPCs still retained their clonogenic and multipotent properties, and their ability to form tendon-like tissues in vivo, thus confirming their self-renewing potential.

Figure 4D:
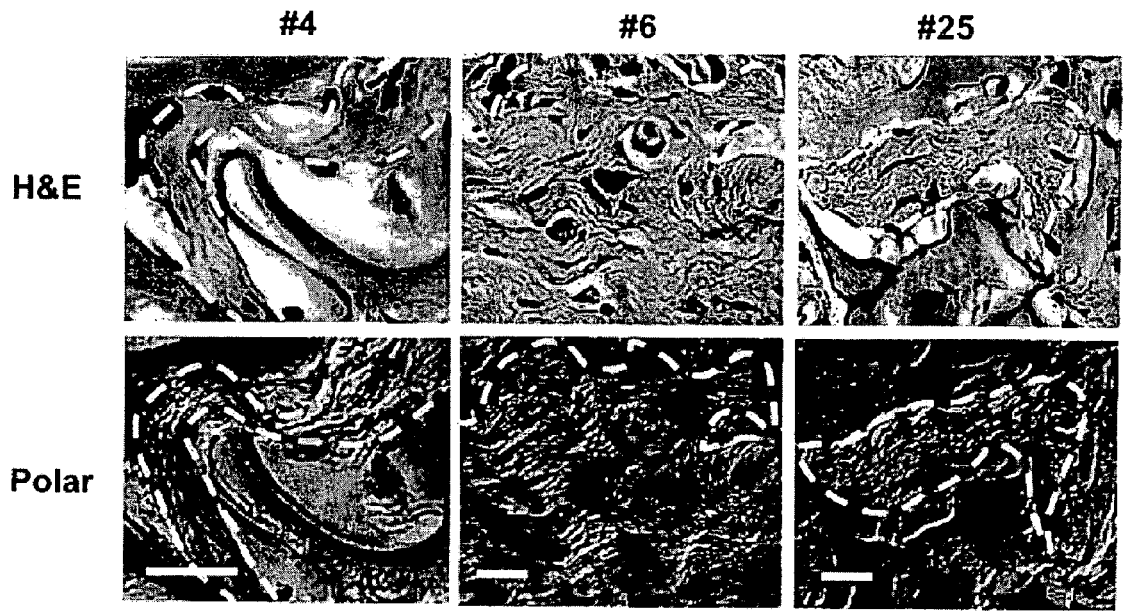
Figure 4E:
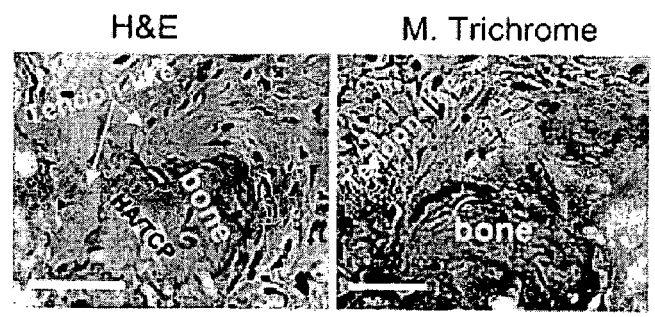
Figure 4F:
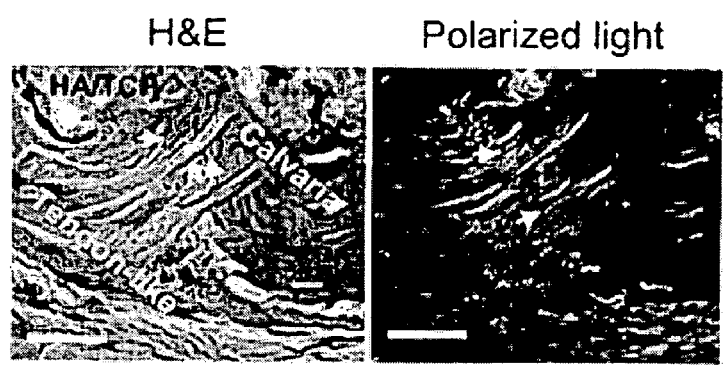

The putative tendon stem cells formed tissues that resembled tendon and attached to bone similar to an enthesis. The identification of TSPCs with self-renewal capability provided a unique opportunity to test whether damaged or diseased tendons could be repaired or regenerated. To test the feasibility of this approach, GFP-expressing TSPCs were expanded in vitro and then transplanted with different carriers into the dorsal surface of immunocompromised mice. Tendon-like tissues were generated from murine TSPCs using either GELFOAM®, HA/TCP, or MATRIGEL® as carriers (FIGS. 3E, 4A, and 4B). These tissues displayed tendon-specific parallel alignments of collagen-fibers, as evidenced by their ability to reflect polarized light (polar, FIGS. 4A-C). The regenerated tendon-like tissues stained strongly for type I collagen (FIGS. 4A-B) and the donor origin of the cells within the newly formed tendons was confirmed by their positive GFP staining (FIGS. 3E and 4A). Similarly, human TSPCs from the initial culture and from individual colonies could generate tendon-like tissues when transplanted with HA/TCP, or MATRIGEL® (FIGS. 4C-D). When murine TSPCs were treated with BMP2 and then transplanted subcutaneously into the dorsal surface of immunocompromised mice, osteotendinous junction-like structures (entheses) were formed (FIG. 4E). More interestingly, when transplanted with HA/TCP onto the surface of mouse calvariae, human TSPCs formed Sharpey's fibers that were inserted into the bone (FIG. 4F). These observations indicate that TSPCs can be used therapeutically to treat damaged tendon and ruptured bone-tendon junctions, termed enthesopathies, which are caused by overuse or trauma.

Figure 5A:
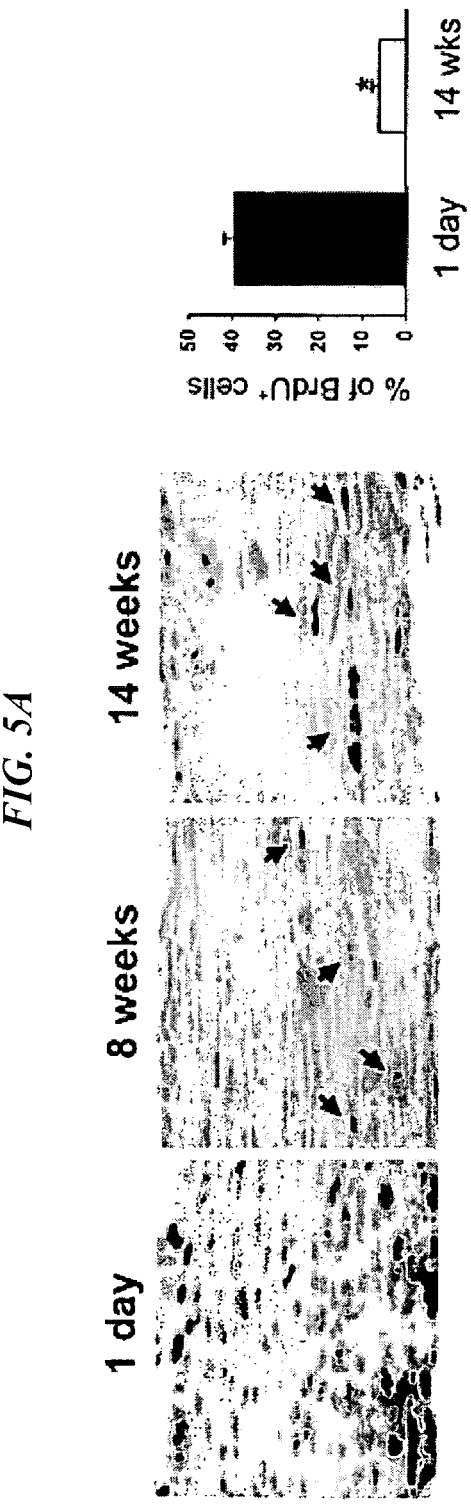
FIGS. 5A-5H illustrate that the extracellular matrix niche dictates the fate of TSPCs.

Extracellular matrix organizes the tendon stem cell niche. Differentiation and self-renewal of stem cells are regulated by their specific niche. To characterize the niche for tendon stem cells, TSPCs were first located within their natural environment based on their slow cycling property. BrdU was administered intraperitoneally into new-born pups (daily for 3 days). Initially, approximately 40% of the cells within the patellar tendon were labeled by BrdU probably due to rapid growth of the skeletal system during this period (FIG. 5A). After an extended period of time (more than 8 weeks), only BrdU label-retaining cells (LRCs), representing stem cells, could be detected. By 14 weeks, only approximately 6% of the cells within the patellar tendon still retained the BrdU label (FIG. 5A), which is a similar frequency to the colony-forming efficiency of tendon-derived cells (FIG. 1A).

This label retaining experiment is universally applied for in vivo stem cell identification, and demonstrated that TSPC reside interior the tendon and surrounded by extracellular matrix. These labeled TSPCs resided in between the long parallel chains of collagen fibrils and were surrounded predominantly by extracellular matrix, indicating that the TSPC niche, comprises primarily various extracellular components. Therefore, alteration in extracellular composition would change the structure of its niche and therefore affect the fate of TSPCs.

Figure 5B:
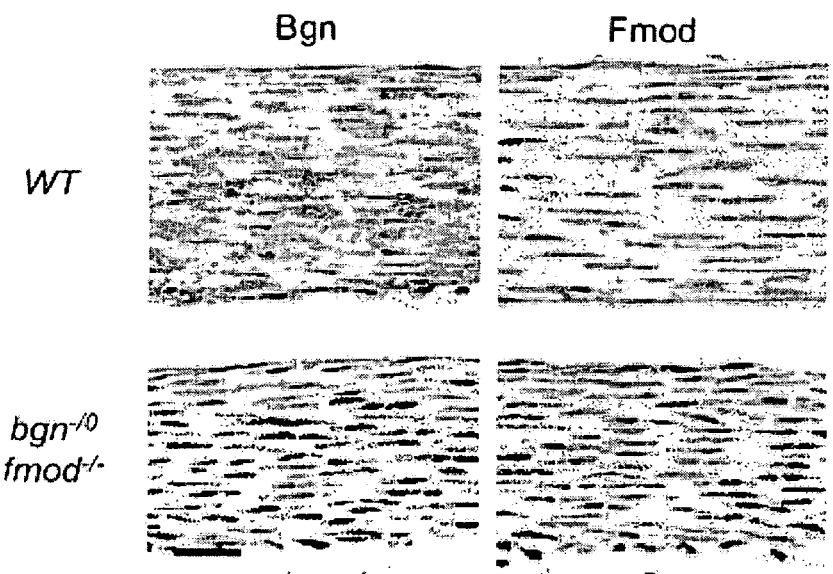
Figure 5C:
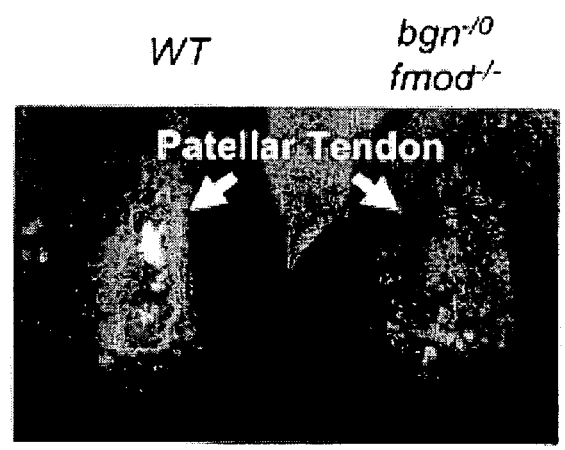
Figure 5D:
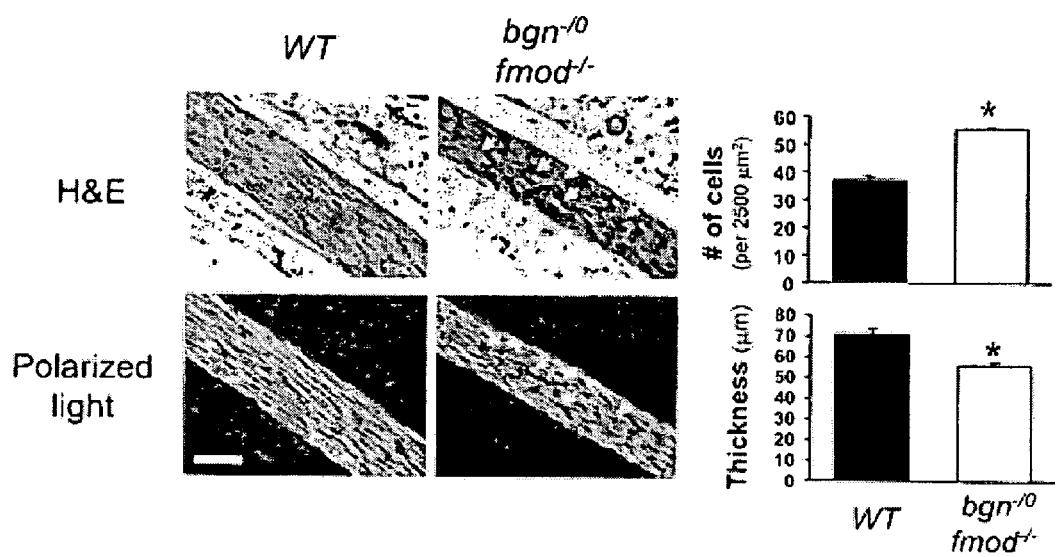
Figure 5E:
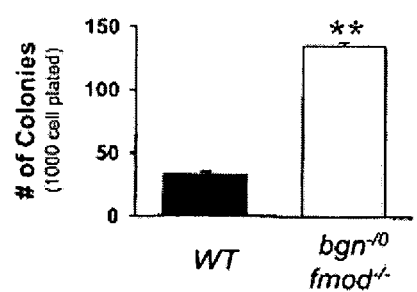
Figure 5F:
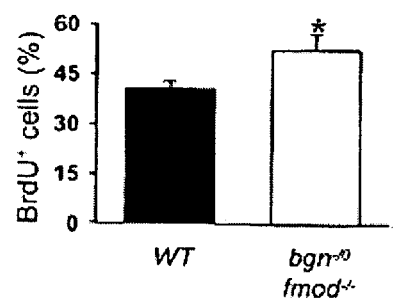
Figure 5G:
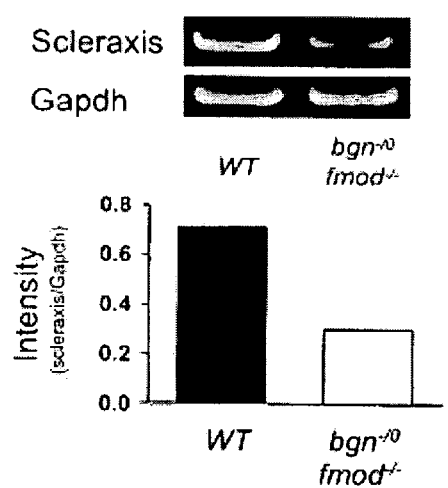
Figure 5H:
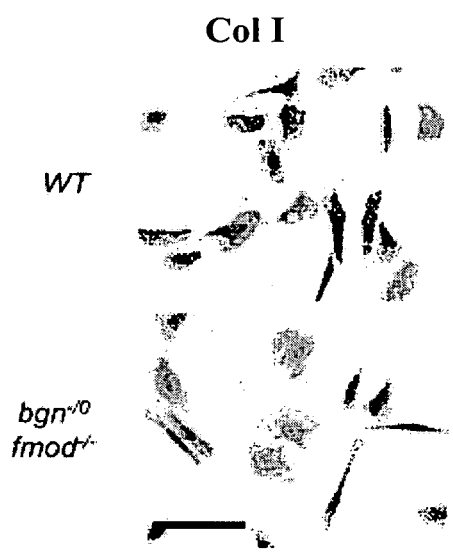

To test this hypothesis, two small proteoglycans, BGN and FMOD were studied, which are highly expressed in tendon (FIG. 5B). Genetic inactivation of BGN and FMOD impairs tendon formation (Ameye et al., Faseb J., 16:673-80 (2002)). The patellar tendon in BGN$^{-/0}$/FMOD$^{-/-}$ mice appeared more translucent (FIG. 5C), significantly thinner, and more cellular than that of WT mice (FIG. 5D). In the absence of BGN and FMOD, the collagen fibers within the tendon were disorganized, judged by the large gaps within the tendon tissue and their appearance under polarized light (FIG. 5D). Based on this observation, it appeared that an ECM-rich niche, organized in part by BGN and FMOD, controls the self-renewal and differentiation of TSPCs. Indeed, the number of TSPCs in BGN$^{-/0}$/FMOD$^{-/-}$ mice was dramatically increased when compared to WT mice (FIG. 5E). TSPCs from bgn.sup.−/0/fmod.sup.−/− mice proliferated faster than the cells from WT mice (FIG. 5F). This increased number and proliferation of TSPCs may reflect a compensation for the impaired differentiation capacity of TSPCs, which could contribute to the malformation of tendon in BGN$^{-/0}$/FMOD$^{-/-}$ mice. This hypothesis was supported by the finding that the expression of the tendon marker, scleraxis, and type I collagen was decreased in TSPCs from BGN$^{-/0}$/FMOD$^{-/-}$ mice compared to cells from WT mice (FIGS. 5G-H).

These results indicated that a TSPC niche, formed predominantly by the extracellular matrix, controls TSPC self-renewal and differentiation, and that alteration of the extracellular matrix composition may lead to tendon malformation and pathologic ossification.

Figure 6A:
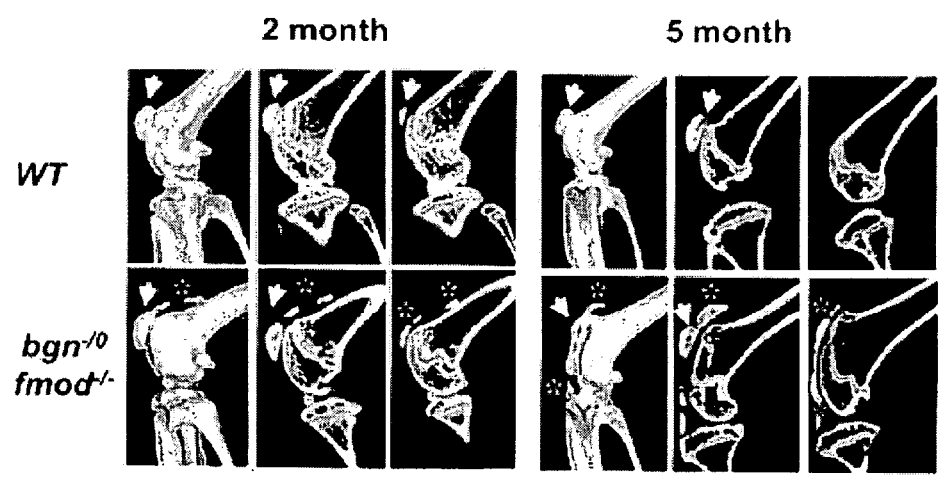
FIGS. 6A-6I show that ectopic activation of BMP signaling induces ossification in $BGN^{-/0}/FMOD^{-/-}$ mice tendon.
Figure 6B:
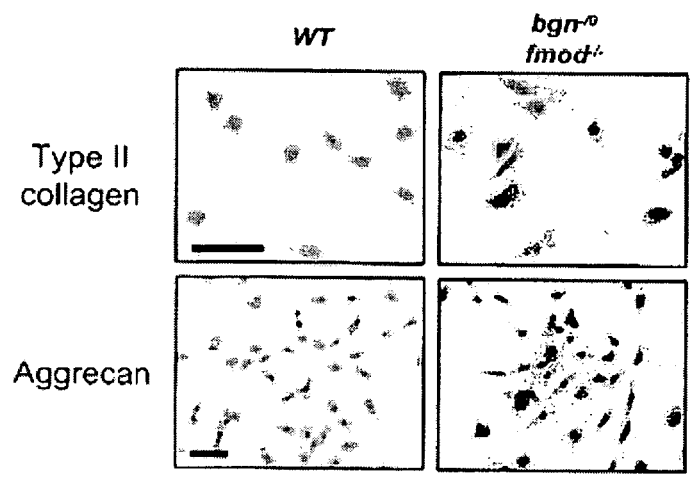
Figure 6C:
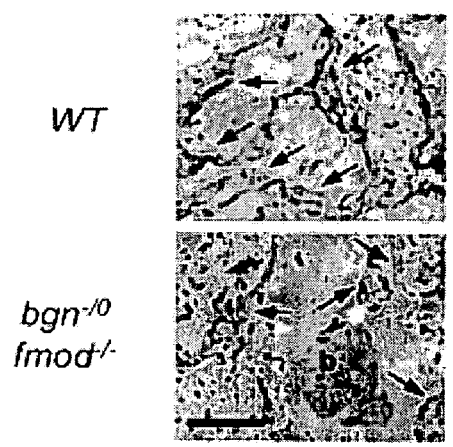
Figure 6D:
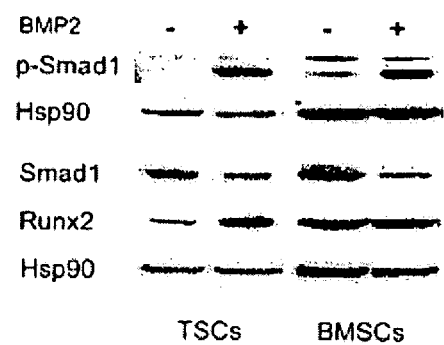
Figure 6E:
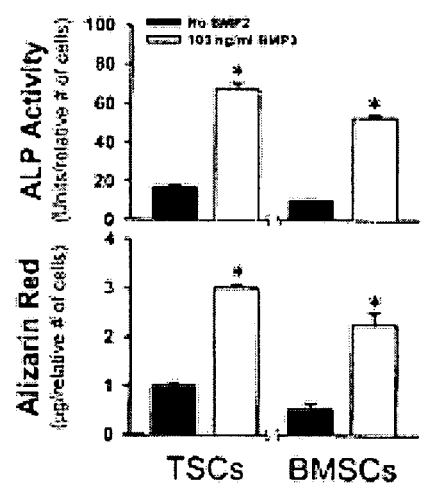
Figure 6F:
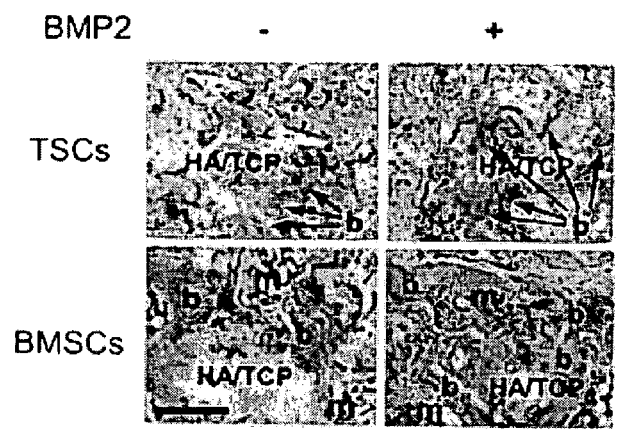
Figure 6G:
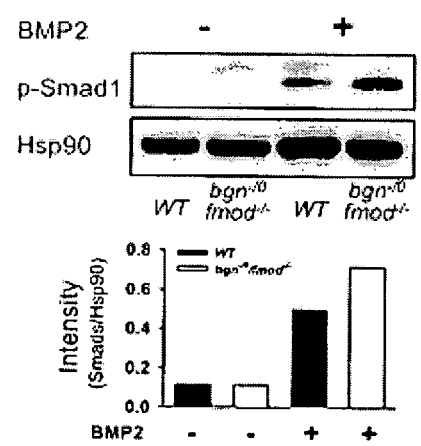
Figure 6H:
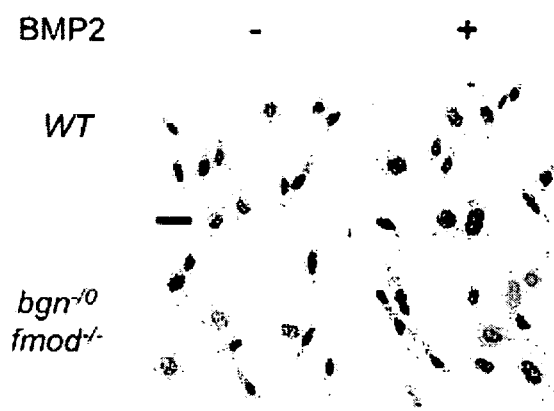
Figure 6I:
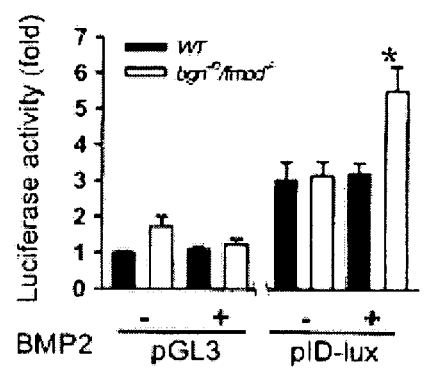
Figure 7A:
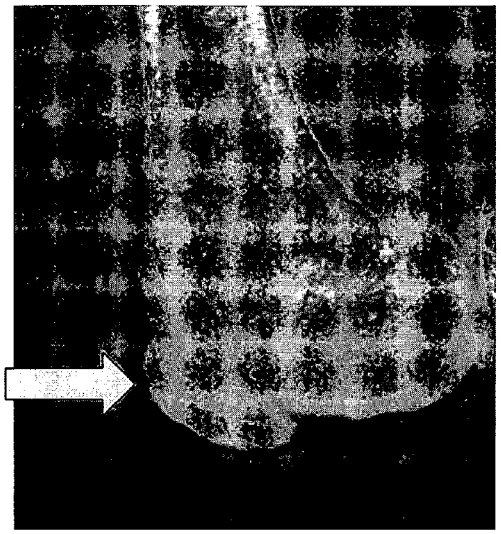
FIGS. 7A and 7B illustrate that ectopic bone ossification occurs to a greater extent in BGN$^{-/0}$/FMOD$^{-/-}$ mice than in wild type mice and that exercise can counteract or inhibit such ectopic bone formation.
Figure 7A:
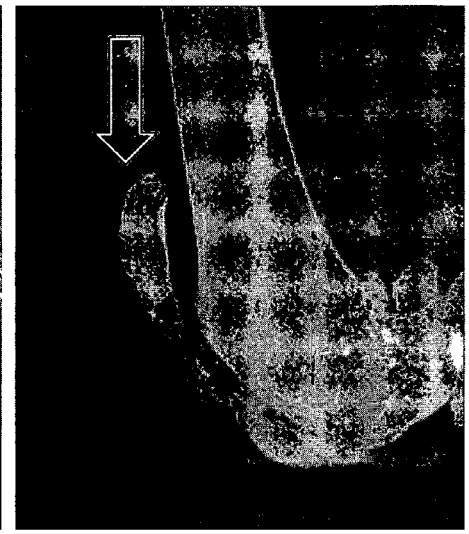
Figure 7B:
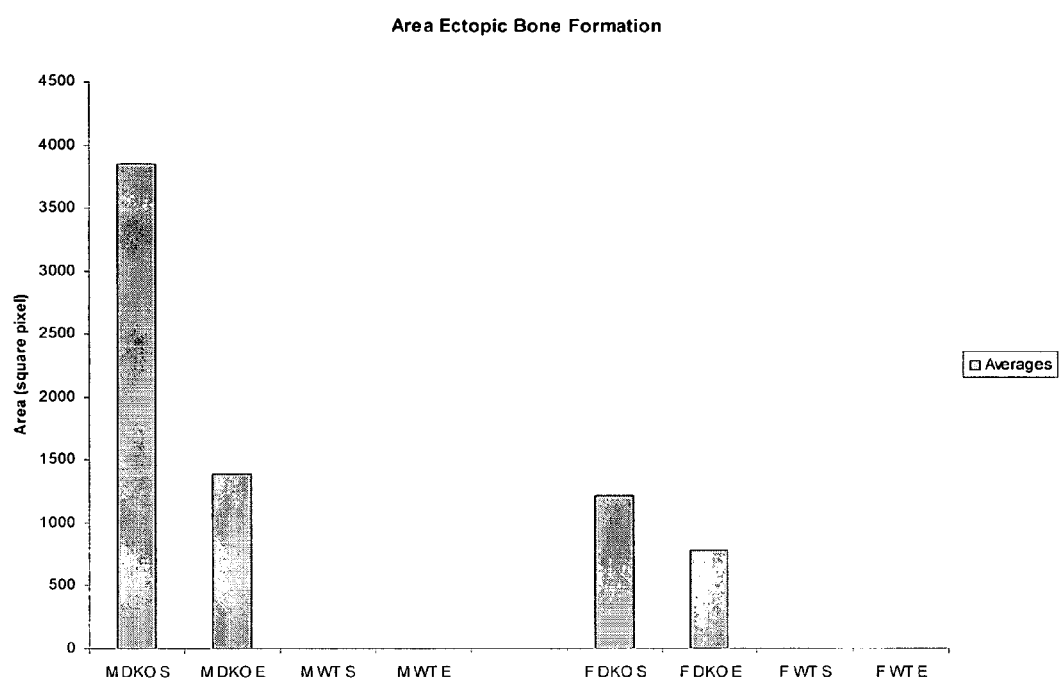

The ECM-rich niche controls TSPC fate by modulating BMP signaling. Human tendon tissue subjected to overuse and injures can acquire ectopic ossification (Fenwick et al., Rheumatology, 41:474-476 (2002)), which might be caused by interruption of the ECM structure and subsequently, the TSPC niche. Indeed, the impaired tendon in BGN$^{-/0}$/FMOD$^{-/-}$ mice undergoes ossification as early as 2 months after birth and became more pronounced with age (FIG. 6A). Similar to intratendinous ossification in human, ossicles formed in tendon of BGN$^{-/0}$/FMOD$^{-/-}$ mice were surrounded by fibrocartilage, suggesting that ossification occurred through endonchondral bone formation (Fenwick et al., Rheumatology, 41:474-476 (2002); Ameye et al., Faseb J., 16:673-680 (2002)). Consistent with this interpretation, BGN$^{-/0}$/FMOD$^{-/-}$ TSPC cultures, but not WT cultures, contained type II collagen-expressing cells (FIG. 6B). The intensity of aggrecan expression, a chondrocyte marker, was also increased in TSPCs in the absence of BGN and FMOD (FIG. 6B). The TSPCs from BGN$^{-/0}$/FMOD$^{-/-}$ mice formed bone in addition to tendon-like tissue in vivo, whereas WT TSPCs only formed tendon-like tissue (FIG. 6C). These results suggest that changes in the TSPC niche-associated extracellular matrix composition may perturb certain cytokines and growth factors stored within the extracellular matrix and thus alter the fate of TSPCs from tenogenesis to osteogenesis. One of these regulatory cytokines is BMP2, which signals through the Smad1/5/8 pathway to increase the expression of Runx2/Cbfa1 (FIG. 6D) and as a result, $Ca^{2+}$ accumulation and alkaline phosphatase activity (FIG. 6E), as well as in vivo bone formation were also increased (FIG. 6F). Therefore, tests were performed to ascertain whether the Smad1/5/8/signaling transduction pathway was affected by the absence of BGN and FMOD. Western blot analysis showed that phosphorylation of Smad1 was greater in BGN$^{-/0}$/FMOD$^{-/-}$ mice TSPCs than in WT cells upon treatment with BMP2 (FIG. 6G). Immunocytochemistry staining revealed more abundant nuclear localization of phosphorylated Smad1 in BGN$^{-/0}$/FMOD$^{-/-}$ TSPCs compared to WT cells, and the difference was even greater upon the stimulation of BMP2 (FIG. 6H). Furthermore, transcriptional activity of BMP responsive luciferase reporter construct (pID-lux) was higher in BGN$^{-/}$o/FMOD$^{-/-}$ TSPCs in the presence of BMP2 (FIG. 6I). These results indicate that BMP signaling was more active in the absence of both BGN and FMOD.

Accordingly, a unique cell population has successfully been identified and isolated from human and mouse tendon tissues that, based on a number of different criteria, exhibits phenotypic characteristics of stem cells. A DNA labeling-retention assay has been used to identify putative stem cells in various tissues. Cotsarelis et al., Cell, 61:1329-1337 (1990); Morris et al., Cell Prolif., 27:279-289 (1994); Booth et al., J. Clin. Invest., 105:1493-1499 (2000). This DNA labeling-retention assay showed that TSPCs reside within a niche environment that is surrounded predominantly by ECM proteins, thus suggesting that the ECM may play a major role in organizing the TSPC niche. Observation of TSPCs from mice deficient in BGN and FMOD indicate that the fate of TSPCs is controlled by specific components of this ECM-rich niche.

The isolation and characterization of TSPCs is highly significant because they provide a new therapeutic agents for treating and repairing injured and/or diseased tendons and ligaments in vivo.

A combination of RT-PCR, immunocytochemistry and FACS analyses was used to characterize the TSPCs. Like other stem cells, no single marker could reliably identify TSPCs. Instead, a combination of factors is used. Although TSPCs expressed many of the same markers as BMSCs, the expression patterns were not identical. TSPCs expressed high levels of tendon-related factors, such as scleraxis, tenomodulin, COMP and tenascin C. Murine TSPCs expressed CD90.2, a fibroblast marker, but not CD18, a BMSC marker. These data suggest that TSPCs are closely related to BMSCs, but not identical.

The stem cell niche has been defined as a specialized microenvironment that houses stem cells and maintains a balance of quiescence, self-renewal and cell fate commitment. The stem cell niche is a three-dimensional structure composed of cells, cytokines and the extracellular matrix. A number of stem cell niches have been identified within a variety of tissues and organs. For example, the osteoblasts govern the hematopoietic stem cell niche through the BMP, PTH, and the Tie2/angiopoietin-1 signaling pathways. The bulge of the hair follicle, crypt and perivascular region provides a niche microenvironment for epidermal, intestinal and neural stem cells, respectively, perhaps through multiple signaling pathways. In addition, the perivascular region was also identified as the niche that maintains the sternness of bone marrow mesenchymal stem cells (MSCs).

In this study, the inventors have shown that the tendon stem cell niche is composed predominantly of extracellular matrix and that alteration of its composition changes TSPC pool size, and detours TSPC fate from tenogenesis to osteogenesis, leading to ectopic ossification in the tendon of BGN$^{-/0}$/FMOD$^{-/-}$ mice. Extracellular matrix proteins, including proteoglycans, regulate the fate of the stem cells within their niche by modulating the bioactivities of growth factors and cytokines that they often bind to. In fact, tenascin C affects neuronal differentiation by modulating the sensitivity of the stem cells to FGF2 and BMP4. The data shown herein also showed TSPCs exhibit increased sensitivity to BMP2 in the absence of BGN and FMOD, which according to the invention is a mechanistic basis for altering the fate of TSPCs. BMP signaling has been shown to inhibit tendon formation during development. These observations reveal new and important roles for the extracellular matrix microenvironment in maintaining TSPCs and in orchestrating normal tissue development and maintenance.

The discovery of stem cells from tendon that possess regenerative capability opens new possibilities to treat damaged tendon tissue that is slow to repair after injury. Unlike autologous bone grafts that can be harvested in large quantities from large bones like the pelvis, autologous tendon for use as grafting material is not readily available. However, because the tendon stem cells of the invention have the ability to replicate both in vitro and in vivo, isolation of cells from just a small portion of tendon can lead an expanded cell population that subsequently could also form sufficient tendon tissue to replace/repair injured and diseased tendons and ligament. Moreover, the tendon stem cells have the capacity to integrate into bone, thereby offering new therapeutic strategies to improve the current means of tendon repair.

In addition, as described herein, TSPCs isolated from human tendons formed tendon-like tissue and enthesis-like structures (i.e., bone-tendon junctions) when transplanted into immunocompromised mice. These data suggest that human TSPC could eventually be used to treat patients with damaged tendon or ruptured bone-tendon junctions (enthesopathies) that is commonly caused by tendon overuse or trauma. These TSPCs could also provide new ways to study entheseal pathophysiology, an area that remains poorly understood.

Previous studies have indicated that BMSCs could form tendon/ligament-type structures (Awad et al., Tissue Eng., 5:267-277 (1999)). However, a molecular characterization of these cells showed that they different from TSCs, and they formed bone rather than tendon-like tissue when in vitro expanded cells were transplanted into mice. Therefore, the repair and regeneration of tendon, using BMSCs without differential induction, could potentially lead to ossification, thereby worsening the tendinopathy (Rooney et al., Matrix, 12:274-281 (1992); Rooney et al., J. Pathol., 169:375-381 (1993); Harris et al., J. Orthop. Res., 22:998-1003 (2004)).

Example 3

Tendon Stem Cell Fate Controlled by the Extracellular Matrix and by Physical Exercise This Example shows that exercise (treadmill running) as well as the extra-cellular matrix influences the fate of tendon stem cells.

Methods

The mouse models described in the foregoing examples were used to assess the role of biomechanical force and extracellular matrix components (biglycan and fibromodulin) and in modulating the fate of the tendon stem cells in vivo. Wild type and $BGN^{-/0}/FMOD^{-/-}$ mice were subjected to treadmill running and the levels of ectopic ossification were assessed using X-ray analysis.

Results

Preliminary results confirmed the importance of the extracellular matrix components (biglycan and fibromodulin) in regulating ectopic ossification and tendon stem cell fate. In particular, when normal and mutant mice were subjected to a mild 30 day running regime it was discovered that there was a decrease in the level of ectopic bone formed in the mutant mice. Wild type mice were not affected by exercise. However, a gender bias was observed in that loss of extracellular matrix components (biglycan and fibromodulin) affected males to a greater extent than females. These data indicate that both the extra-cellular matrix and forced treadmill running can control the fate of tendon stem cells.

BIBLIOGRAPHY

Sharma, P. & Maffulli, N. J Musculoskelet Neuronal Interact 6, 18 1-90 (2006).
Kannus, P. Scand J Med Sci Sports 10, 3 12-20 (2000).
Yoon, J. H. & Halper, J. J Musculoskelet Neuronal Interact 5, 22-34 (2005).
Fenwick, S. et al. Rheumatology (Oxford) 41, 474-6 (2002).
Salingcarnboriboon, R. et al. Exp Cell Res 287, 289-300 (2003).
Seo, B. M. et al. Lancet 364, 149-55 (2004).
Fuchs, E., Tumbar, T. & Guasch, G. Cell 116, 769-78 (2004).
Taichman, R. S. & Emerson, S. G. J Exp Med 179, 1677-82 (1994).
Zhang, J. et al. Nature 425, 836-41 (2003).
Calvi, L. M. et al. Nature 425, 841-6 (2003).
Shen, Q. et al. Science 304, 1338-40 (2004).
Shi, S. & Gronthos, S. J Bone Miner Res 18, 696-704 (2003).
Doherty, M. J. et al. J Bone Miner Res 13, 828-38 (1998).
Brent, A. E., Schweitzer, R. & Tabin, C. J. Cell 113, 235-48 (2003).
DiCesare, P. E., et al. Eur J Biochem 223, 927-37 (1994).
Ahyama, H., et al. Genes Dev 16, 2813-28 (2002).
Komori, T. et al. Cell 89, 755-64 (1997).
Nakashima, K. et al. Cell 108, 17-29 (2002).
Brandau, O., et al. Dev Dyn 221, 72-80 (2001).
Spangrude, G. J., Heimfeld, S. & Weissman, I. L. Science 241, 58-62 (1988).
Van Vlasselaer, P., Falla, N., Snoeck, H. & Mathieu, E. Blood 84, 753-63 (1994).
Gussoni, E. et al. Nature 401, 390-4 (1999).
Tarnalci, T. et al. J Cell Biol 157, 571-7 (2002).
Welm, B. E. et al. Dev Biol 245, 42-56 (2002).
Miura, Y. et al. Proc Natl Acad Sci USA 102, 14022-7 (2005).
Simmons, P. J. & Torok-Storb, B. Blood 78, 55-62 (1991).
Filshie, R. J. et al. Leukemia 12, 414-21 (1998).
Kuznetsov, S. A. et al. J Bone Miner Res 12, 1335-47 (1997).
Bi, Y. et al. J Biol Chem (2005).
Krebsbach, P. H. et al. Transplantation 63, 1059-69 (1997).
Bickenbach, J. R. J Dent Res 60 Spec No C, 161 1-20 (1981).
Ameye, L. et al. Faseb J 16, 673-80 (2002).
Cotsarelis, G., Sun, T. T. & Lavker, R. M. Cell 61, 1329-37 (1990).
Morris, R. J. & Potten, C. S. Cell Prolif 27, 279-89 (1994).
Booth, C. & Potten, C. S. J Clin Invest 105, 1493-9 (2000).
Scadden, D. T. Nature 441, 1075-9 (2006).
Krause, D. S. Oncogene 21, 3262-9 (2002).
Arai, F. et al. Cell 118, 149-61 (2004).
Moore, K. A. & Lemischka, I. R. Science 311, 1880-5 (2006).
Blanpain, C. & Fuchs, E. Annu Rev Cell Dev Biol. 22, 339-73 (2006).
Garcion, E., et al. C. Development 131, 3423-32 (2004).
Nilsson, S. K. et al. Blood 106, 1232-9 (2005).
Ohta, M., Sakai, T., Saga, Y., Aizawa, S. & Saito, M. Blood 91, 4074-83 (1998).
Stier, S. et al. J Exp Med 201, 1781-91 (2005).
Schweitzer, R. et al. Development 128, 3855-66 (2001).
Awad, H. A. et al. Tissue Eng 5, 267-77 (1999).
Rooney, P., Grant, M. E. & McClure, J. Matrix 12, 274-81 (1992).
Rooney, P., Walker, D., Grant, M. E. & McClure, J. J Pathol 169, 375-81 (1993).
Harris, M. T. et al. J Orthop Res 22, 998-1003 (2004).
Caplan, A. I. & Dennis, J. E. J Cell Biochem 98, 1076-84 (2006).
Robey, P. G. J Clin Invest 105, 1489-91 (2000).
Dezawa, M. et al. J Clin Znvest 113, 1701-10 (2004).
Dezawa, M. et al. Science 309, 314-7 (2005).
Hoffmann, A. et al. J Clin Znvest 116, 940-52 (2006).
Kuznetsov, S. A., Friedenstein, A. J. & Robey, P. G. Br J Haematol 97, 561-70 (1997).
Gimble, J. M. et al. J Cell Biochem 58, 393-402 (1995).
Johnstone, B., et al. Exp Cell Res 238, 265-72 (1998).
Kostenuik, P. J., et al. Am J Physiol 273, E1133-9 (1997).
Lopez-Rovira, T., et al. J Biol Chem 277, 3 176-85 (2002).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A composition comprising an isolated tendon stem cell or cells, wherein the stem cell(s) are isolated from tendon tissue, and wherein the stem cell(s) express CD44, Stro-1, CD146 and/or CD90 or any combination thereof.

2. The composition of claim 1, wherein said composition comprises an enriched population of isolated stem cells, wherein the stem cells are enriched from an extracellular matrix niche within tendon tissue, and can give rise to progeny consisting of two or more tissue types, wherein at least one of the tissue types is tendon.

3. The composition of claim 1, wherein the stem cell(s) are non-embryonic stem cells that can differentiate into tendon tissue in vivo.

4. The composition of claim 1 wherein the stem cell(s) are adult stem cells.

5. The composition of claim 1 wherein the stem cell(s) are isolated from the tendon tissue extracellular matrix.

6. The composition of claim 1 wherein the stem cell(s) remain undifferentiated in culture.

7. The composition of claim 1 wherein the stem cell(s) differentiate into tendon tissue or tendon cells when in contact with extracellular matrix components in vivo.

8. The composition of claim 1 wherein the stem cell(s) differentiate into tendon tissue or tendon cells in vitro.

9. The composition of claim 8, wherein the tendon tissue can attach to bone.

10. The composition of claim 1, wherein the stem cell(s) can differentiate into ligament.

11. The composition of claim 1, wherein the stem cell(s) can differentiate into bone-producing cells.

12. The composition of claim 1, wherein the stem cell(s) differentiate into bone-producing cells when exposed to bone morphogenetic protein 2 (BMP2).

13. The composition of claim 1, wherein the stem cell(s) can give rise to osteogenesis, adipogenesis, chondrogenesis, or any combination thereof, in a mammal.

14. The composition of claim 1, wherein the stem cell(s) express higher levels of scleraxis, tenomodulin and/or tenascin C than bone marrow stromal cells.

15. The composition of claim 1, wherein the stem cell(s) express insignificant/minimal levels of CD34 (a hematopoietic stem cell marker), CD117 (a hematopoietic stem cell marker), CD45 (a leukocyte marker), c-kit (an endothelial cell marker), CD106 (an endothelial cell marker), CD18 (bone marrow stromal cell marker), and/or any combination thereof.

16. The composition of claim 1, wherein the stem cell(s) express stem cell antigen-1 (Sca-1).

17. A composition comprising a carrier and the composition of claim 1.

18. The composition of claim 17, further comprising an effective amount of biglycan and/or fibromodulin.

19. The composition of claim 18, wherein the effective amount allows expansion of the tendon stem cells while inhibiting differentiation of at least a portion of the tendon stem cells.

20. The composition of claim 17, wherein the carrier comprises a culture medium.

21. The composition of claim 17, wherein the carrier comprises a saline solution, a buffered saline solution, gelatin, polyvinyl sponges, collagen, hydroxyapatite/tricalcium phosphate and/or extracellular matrix.

* * * * *

SEQUENCE LISTING

```
<160> NUMBER OF SEQ ID NOS: 55

<210> SEQ ID NO 1
<211> LENGTH: 368
<212> TYPE: PRT
<213> ORGANISM: Homo sapiens

<400> SEQUENCE: 1

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
                20                  25                  30

Pro Phe Met Met Asn Asp Glu Glu Ala Ser Gly Ala Asp Thr Ser Gly
                35                  40                  45

Val Leu Asp Pro Asp Ser Val Thr Pro Thr Tyr Ser Ala Met Cys Pro
        50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
                100                 105                 110

Leu Gln His Leu Tyr Ala Leu Val Leu Val Asn Asn Lys Ile Ser Lys
            115                 120                 125

Ile His Glu Lys Ala Phe Ser Pro Leu Arg Lys Leu Gln Lys Leu Tyr
        130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
                180                 185                 190

Asn Pro Leu Glu Asn Ser Gly Phe Glu Pro Gly Ala Phe Asp Gly Leu
            195                 200                 205

Lys Leu Asn Tyr Leu Arg Ile Ser Glu Ala Lys Leu Thr Gly Ile Pro
```

```
                  210                 215                 220
Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
                260                 265                 270

Leu Ser Phe Leu Pro Thr Leu Arg Glu Leu His Leu Asp Asn Asn Lys
                275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
                340                 345                 350

Arg Cys Val Thr Asp Arg Leu Ala Ile Gln Phe Gly Asn Tyr Lys Lys
                355                 360                 365

<210> SEQ ID NO 2
<211> LENGTH: 2422
<212> TYPE: DNA
<213> ORGANISM: Homo sapiens

<400> SEQUENCE: 2
aattcggcat gagggagtg agtagctgct ttcggtccgc cggacacacc ggacagatag      60
acgtgcggac ggcccaccac cccagccctc caactagtca gcctgcgcct ggcgcctccc     120
ctctccaggt ccatccgcca tgtggcccct gtggcgcctc gtgtctctgc tggccctgag     180
ccaggccctg ccctttgagc agagaggctt ctgggacttc accctggacg atgggccatt     240
catgatgaac gatgaggaag cttcgggcgc tgacacctca ggcgtcctgg acccggactc     300
tgtcacaccc acctcagcg ccatgtgtcc tttcggctgc cactgccacc tgcgggtggt     360
tcagtgctcc gacctgggtc tgaagtctgt gcccaaagag atctcccctg acaccacgct     420
gctggacctg cagaacaacg acatctccga gctccgcaag gatgacttca agggtctcca     480
gcacctctac gccctcgtcc tggtgaacaa caagatctcc aagatccatg agaaggcctt     540
cagcccactg cggaagctgc agaagctcta catctccaag aaccacctgg tggagatccc     600
gcccaaccta cccagctccc tggtggagct ccgcatccac gacaaccgca tccgcaaggt     660
gcccaaggga gtgttcagcg ggctccggaa catgaactgc atcgagatgg cgggaaaccc     720
actggagaac agtggctttg aacctggagc cttcgatggc ctgaagctca actacctgcg     780
catctcagag gccaagctga ctggcatccc caaagacctc cctgagaccc tgaatgaact     840
ccacctagac cacaacaaaa tccaggccat cgaactggag gacctgcttc gctactccaa     900
gctgtacagg ctgggcctag ccacaaccaa gatcaggatg atcgaaacgg ggagcctgag     960
cttcctgccc accctccggg agctccactt ggacaacaac aagttggcca gggtgccctc    1020
agggctccca gacctcaagc tcctccaggt ggtctatctg cactccaaca acatcaccaa    1080
agtgggtgtc aacgacttct gtcccatggg cttcggggtg aagcgggcct actacaacgg    1140
catcagcctc ttcaacaacc ccgtgcccta ctgggaggtg cagccggcca ctttccgctg    1200
cgtcactgac cgcctggcca tccagtttgg caactacaaa agtagaggc agctgcagcc    1260 accgcggggc ctcagtgggg gtctctgggg aacacagcca gacatcctga tggggaggca    1320
```

```
gagccaggaa gctaagccag ggcccagctg cgtccaaccc agcccccac ctcgggtccc    1380 tgaccccagc tcgatgcccc atcaccgcct ctccctggct cccaagggtg caggtgggcg    1440
caaggcccgg cccccatcac atgttcccTT ggcctcagag ctgcccctgc tctcccacca    1500
cagccaccca gaggcacccc atgaagcttt tttctcgttc actcccaaac ccaagtgtcc    1560
aaggctccag tcctaggaga acagtccctg ggtcagcagc caggaggcgg tccataagaa    1620
tggggacagt gggctctgcc agggctgccg cacctgtcca gacacacatg ttctgttcct    1680
cctcctcatg catttccagc cttTcaaccc tccccgactc tgcggctccc ctcagccccc    1740
ttgcaagttc atggcctgtc cctcccagac ccctgctcca ctggcccttc gaccagtcct    1800
cccttctgtt ctctctttcc ccgtccttcc tctctctctc tctctctctc tctctctctt    1860
tctgtgtgtg tgtgtgtgtg tgtgtgtgtg tgtgtgtgtg tcttgtgctt cctcagacct    1920
ttctcgcttc tgagcttggt ggcctgttcc ctccatctct ccgaacctgg cttcgcctgt    1980
cccttTcact ccacaccctc tggccttctg ccttgagctg ggactgcttt ctgtctgtcc    2040
ggcctgcacc cagcccctgc ccacaaaacc ccagggacag cggtctcccc agcctgccct    2100
gctcaggcct tgcccccaaa cctgtactgt cccggaggag gttgggaggt ggaggcccag    2160
catcccgcgc agatgacacc atcaaccgcc agagtcccag acaccggttt tcctagaagc    2220
ccctcaccCc cactggccca ctggtggcta ggtctcccct tatccttctg gtccagcgca    2280
aggaggggct gcttctgagg tcggtggctg tctttccatt aaagaaacac cgtgcaacgt    2340
gaaaaaaaaa aaaaaaaaaa aaaaaaaaaa aaaaaaaaaa aaaaaaaaaa aaaaaaaaaa    2400
aaaaaaaaaa aaaccctcg gg                                              2422

<210> SEQ ID NO 3
<211> LENGTH: 376
<212> TYPE: PRT
<213> ORGANISM: Homo sapiens

<400> SEQUENCE: 3

Met Gln Trp Ala Ser Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Leu Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
        115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175
```

```
Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asp Glu Ile Gln Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Val Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile
    370                 375

<210> SEQ ID NO 4
<211> LENGTH: 1247
<212> TYPE: DNA
<213> ORGANISM: Homo sapiens

<400> SEQUENCE: 4
cggaattcaa gaaacacaaa atgcagtggg cgtccctcct gctgctggca gggctcttct      60
ccctctccca ggcccagtat gaagatgacc ctcattggtg gttccactac ctccgcagcc     120
agcagtccac ctactacgat ccctatgacc cttacccgta tgagacctac gagccttacc     180
cctatgggt ggatgaaggg ccagcctaca cctacggctc ccatcccct ccagatcccc      240
gcgactgccc ccaggaatgc gactgcccac ccaacttcct cacggccatg tactgtgaca     300
atcgcaacct caagtacctg cccttcgttc cctcccgcat gaagtatgtg tacttccaga     360
acaaccagat cacctccatc aggaaggcg tctttgacaa tgccacaggg ctgctctgga     420
ttgctctcca cggcaaccag atcaccagtg ataaggtggg caggaaggtc ttctccaagc     480
tgaggcacct ggagaggctg tacctggacc acaacaacct gacccggatg cccgtcccc      540
tgcctcgatc cctgagagag ctccatctcg accacaacca gatctcacgg gtccccaaca     600
atgctctgga ggggctggag aacctcacgg ccttgtacct ccaacacgat gagatccagg     660
aagtgggcag ttccatgagg ggcctccggt cactgatctt gctggacctg agttataacc     720
accttcggaa ggtgcctgat gggctgccct cagctcttga gcagctgtac atggagcaca     780
acaatgtcta caccgtcccc gatagctact tccgggggc gcccaagctg ctgtatgtgc     840
ggctgtccca acagtctca accaacaatg gcctggcctc caacaccttc aattccagca     900
gcctccttga gctagacctc tcctacaacc agctgcagaa gatccccca gtcaacacca     960
acctggagaa cctctacctc caaggcaata ggatcaatga gttctccatc agcagcttct    1020
```

-continued

```
gcaccgtggt ggacgtcgtg aacttctcca agctgcaggt cgtgcgcctg acgggaacg    1080 agatcaagcg cagcgccatg cctgccgacg cgcccctctg cctgcgcctt gccagcctca    1140
tcgagatctg agcagccctg caccgggta ctgggcggag agcccccgtg catttggct     1200 tgatggtttg gtttggctta tggaagatct gggacagacc gtgtgac                  1247
```

<210> SEQ ID NO 5
<211> LENGTH: 396
<212> TYPE: PRT
<213> ORGANISM: Homo sapiens

<400> SEQUENCE: 5

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335
```

-continued

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 6
<211> LENGTH: 373
<212> TYPE: PRT
<213> ORGANISM: Homo sapiens

<400> SEQUENCE: 6

Leu Val Pro Glu Leu Gly Arg Arg Lys Phe Ala Ala Ser Ser Gly
1               5                   10                  15

Arg Pro Ser Ser Gln Pro Ser Asp Glu Val Leu Ser Glu Phe Glu Leu
            20                  25                  30

Arg Leu Leu Ser Met Phe Gly Leu Lys Gln Arg Pro Thr Pro Ser Arg
        35                  40                  45

Asp Ala Val Val Pro Pro Tyr Met Leu Asp Leu Tyr Arg Arg His Ser
    50                  55                  60

Gly Gln Pro Gly Ser Pro Ala Pro Asp His Arg Leu Glu Arg Ala Ala
65                  70                  75                  80

Ser Arg Ala Asn Thr Val Arg Ser Phe His His Glu Glu Ser Leu Glu
                85                  90                  95

Glu Leu Pro Glu Thr Ser Gly Lys Thr Thr Arg Arg Phe Phe Phe Asn
            100                 105                 110

Leu Ser Ser Ile Pro Thr Glu Glu Phe Ile Thr Ser Ala Glu Leu Gln
        115                 120                 125

Val Phe Arg Glu Gln Met Gln Asp Ala Leu Gly Asn Asn Ser Ser Phe
    130                 135                 140

His His Arg Ile Asn Ile Tyr Glu Ile Ile Lys Pro Ala Thr Ala Asn
145                 150                 155                 160

Ser Lys Phe Pro Val Thr Arg Leu Leu Asp Thr Arg Leu Val Asn Gln
                165                 170                 175

Asn Ala Ser Arg Trp Glu Ser Phe Asp Val Thr Pro Ala Val Met Arg
            180                 185                 190

Trp Thr Ala Gln Gly His Ala Asn His Gly Phe Val Val Glu Val Ala
        195                 200                 205

His Leu Glu Glu Lys Gln Gly Val Ser Lys Arg His Val Arg Ile Ser
    210                 215                 220

Arg Ser Leu His Gln Asp Glu His Ser Trp Ser Gln Ile Arg Pro Leu
225                 230                 235                 240

Leu Val Thr Phe Gly His Asp Gly Lys Gly His Pro Leu His Lys Arg
                245                 250                 255

Glu Lys Arg Gln Ala Lys His Lys Gln Arg Lys Arg Leu Lys Ser Ser
            260                 265                 270

Cys Lys Arg His Pro Leu Tyr Val Asp Phe Ser Asp Val Gly Trp Asn
        275                 280                 285

Asp Trp Ile Val Ala Pro Pro Gly Tyr His Ala Phe Tyr Cys His Gly
    290                 295                 300

Glu Cys Pro Phe Pro Leu Ala Asp His Leu Asn Ser Thr Asn His Ala
305                 310                 315                 320

```
Ile Val Gln Thr Leu Val Asn Ser Val Asn Ser Lys Ile Pro Lys Ala
                325                 330                 335

Cys Cys Val Pro Thr Glu Leu Ser Ala Ile Ser Met Leu Tyr Leu Asp
                340                 345                 350

Glu Asn Glu Lys Val Val Leu Lys Asn Tyr Gln Asp Met Val Val Glu
            355                 360                 365

Gly Cys Gly Cys Arg
        370

<210> SEQ ID NO 7
<211> LENGTH: 360
<212> TYPE: PRT
<213> ORGANISM: Homo sapiens

<400> SEQUENCE: 7

Ser Ser Gly Arg Pro Ser Ser Gln Pro Ser Asp Glu Val Leu Ser Glu
1               5                   10                  15

Phe Glu Leu Arg Leu Leu Ser Met Phe Gly Leu Lys Gln Arg Pro Thr
                20                  25                  30

Pro Ser Arg Asp Ala Val Val Pro Pro Tyr Met Leu Asp Leu Tyr Arg
            35                  40                  45

Arg His Ser Gly Gln Pro Gly Ser Pro Ala Pro Asp His Arg Leu Glu
        50                  55                  60

Arg Ala Ala Ser Arg Ala Asn Thr Val Arg Ser Phe His His Glu Glu
65                  70                  75                  80

Ser Leu Glu Glu Leu Pro Glu Thr Ser Gly Lys Thr Thr Arg Arg Phe
                85                  90                  95

Phe Phe Asn Leu Ser Ser Ile Pro Thr Glu Glu Phe Ile Thr Ser Ala
                100                 105                 110

Glu Leu Gln Val Phe Arg Glu Gln Met Gln Asp Ala Leu Gly Asn Asn
            115                 120                 125

Ser Ser Phe His His Arg Ile Asn Ile Tyr Glu Ile Ile Lys Pro Ala
        130                 135                 140

Thr Ala Asn Ser Lys Phe Pro Val Thr Arg Leu Leu Asp Thr Arg Leu
145                 150                 155                 160

Val Asn Gln Asn Ala Ser Arg Trp Glu Ser Phe Asp Val Thr Pro Ala
                165                 170                 175

Val Met Arg Trp Thr Ala Gln Gly His Ala Asn His Gly Phe Val Val
                180                 185                 190

Glu Val Ala His Leu Glu Glu Lys Gln Gly Val Ser Lys Arg His Val
            195                 200                 205

Arg Ile Ser Arg Ser Leu His Gln Asp Glu His Ser Trp Ser Gln Ile
        210                 215                 220

Arg Pro Leu Leu Val Thr Phe Gly His Asp Gly Lys Gly His Pro Leu
225                 230                 235                 240

His Lys Arg Glu Lys Arg Gln Ala Lys His Lys Gln Arg Lys Arg Leu
                245                 250                 255

Lys Ser Ser Cys Lys Arg His Pro Leu Tyr Val Asp Phe Ser Asp Val
                260                 265                 270

Gly Trp Asn Asp Trp Ile Val Ala Pro Pro Gly Tyr His Ala Phe Tyr
            275                 280                 285

Cys His Gly Glu Cys Pro Phe Pro Leu Ala Asp His Leu Asn Ser Thr
        290                 295                 300

Asn His Ala Ile Val Gln Thr Leu Val Asn Ser Val Asn Ser Lys Ile
305                 310                 315                 320
```

```
Pro Lys Ala Cys Cys Val Pro Thr Glu Leu Ser Ala Ile Ser Met Leu
            325                 330                 335

Tyr Leu Asp Glu Asn Glu Lys Val Val Leu Lys Asn Tyr Gln Asp Met
        340                 345                 350

Val Val Glu Gly Cys Gly Cys Arg
        355             360

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
aacacggcct tcactgc                                                  17

<210> SEQ ID NO 9
<211> LENGTH: 17
<212> TYPE: DNA
<213> ORGANISM: Artificial Sequence
<220> FEATURE:
<223> OTHER INFORMATION: Synthetic

<400> SEQUENCE: 9
cttcgaatcg ccgtctt                                                  17

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
cgcagctgca agacgtgaga gagctgt                                       27

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
ccgaattccg ctggtctggg tttcga                                        26

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tcagatgcag tgaggagcac                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ccagccacag cagtgagtaa                                               20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gcagttccca agcatttcat                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cactctggct ttgggaagag                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
aagtgtgtgt gccgtggata                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gtcgagagga ctggggtaca                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
cgatgatgat gacgatggag                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gaggtcctca tctgtggcat                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic

```
<400> SEQUENCE: 20
attttgctca gcattttggg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ctgaagagtc actgcctccc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ccagcaggtt tctctcttgg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ctgggagtct catcctgagc                                              20

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gaagcttgtc tccagtcaaa a                                            21

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
agtcacgcct ttcataacac at                                           22

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ttacaacagg ccaggtttcc                                              20

<210> SEQ ID NO 27
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 27
ctctgggatg gatcgattgt                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gtctggctga cactggacaa                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
tgggccatta gattcctcac                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
gagaggccct atcccaactc                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gtgggtgcag cgaactttat                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
agccatgtac gtagccatcc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ctctcagctg tggtggtgaa                                          20
```

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
agaacatcat ctgggccaac                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tcctctctga gcccttctca                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
ccatgctgga tgagagaggt                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ccaccagtta caaggcatga                                                 20

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
cagttcccaa gcatttcatc c                                               21

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tcaatatggt cgccaaacag                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

```
<400> SEQUENCE: 40
gccagaagct gtgaaacctc                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
gctgcaagct ctccataacc                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
aagaaagggg acccaagaaa                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gtactctctg cctgcccaag                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
tggcaggctc tacacagaga                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
tttcagccgt tctcagaggt                                              20

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
atggagagca aagccctgct c                                            21

<210> SEQ ID NO 47
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 47
gttaggtcca gctggatcga g                                           21

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
tggacaagaa cagcaacgag                                             20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
ttgtcactgg tcagctccag                                             20

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
gcgcacctgg cgcaggcgtc ctg                                         23

<210> SEQ ID NO 51
<211> LENGTH: 22
<212> TYPE: DNA
<213> ORGANISM: Artificial Sequence
<220> FEATURE:
<223> OTHER INFORMATION: Synthetic

<400> SEQUENCE: 51
gcactgcgcg cagcacgtcg ta                                          22

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
ccggagaaca atcagattga agc                                         23

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
cgcctttgct ttggtcagcg g                                           21
```

```
<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
cgaccacttt gtcaagctca                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
aggggtctac atggcaactg                                              20
```